(12) United States Patent
Fujiyoshi et al.

(10) Patent No.: US 9,835,732 B2
(45) Date of Patent: Dec. 5, 2017

(54) RADIATION IMAGING APPARATUS AND RADIATION IMAGING SYSTEM

(71) Applicant: CANON KABUSHIKI KAISHA, Tokyo (JP)

(72) Inventors: Kentaro Fujiyoshi, Tokyo (JP); Minoru Watanabe, Honjo (JP); Keigo Yokoyama, Honjo (JP); Masato Ofuji, Takasaki (JP); Jun Kawanabe, Kumagaya (JP); Hiroshi Wayama, Saitama (JP); Kazuya Furumoto, Saitama (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 70 days.

(21) Appl. No.: 14/696,976

(22) Filed: Apr. 27, 2015

(65) Prior Publication Data
US 2015/0316661 A1 Nov. 5, 2015

(30) Foreign Application Priority Data

May 1, 2014 (JP) .................................. 2014-094875
Mar. 23, 2015 (JP) .................................. 2015-060021

(51) Int. Cl.
*H05G 1/64* (2006.01)
*G01T 1/20* (2006.01)
(Continued)

(52) U.S. Cl.
CPC .......... *G01T 1/2018* (2013.01); *A61B 6/4208* (2013.01); *H01L 27/14609* (2013.01);
(Continued)

(58) Field of Classification Search
CPC ......... G01T 1/00; G01T 1/003; G01T 1/2006; G01T 1/2008; G01T 1/20; G01T 1/24;
(Continued)

(56) References Cited

U.S. PATENT DOCUMENTS 7,205,547 B2   4/2007   Ishii et al. ............... 250/370.09
7,381,963 B2   6/2008   Endo et al. .............. 250/370.09
(Continued)

FOREIGN PATENT DOCUMENTS

EP   1227662   7/2002
EP   1341375   9/2003
(Continued)

OTHER PUBLICATIONS

U.S. Appl. No. 14/729,248, filed Jun. 3, 2015.
(Continued)

*Primary Examiner* — Jason McCormack
(74) *Attorney, Agent, or Firm* — Fitzpatrick, Cella, Harper & Scinto

(57) ABSTRACT

A radiation imaging apparatus has a plurality of pixels including a plurality of imaging pixels for obtaining a radiation image and a detecting pixel for detecting radiation, a plurality of column signal lines, and a detection signal line corresponding to the detecting pixel. Each of the imaging pixels includes a first conversion element configured to convert radiation into an electrical signal, and a first switch arranged between the first conversion element and a corresponding column signal line among the plurality of column signal lines. The detecting pixel includes a second conversion element configured to convert radiation into an electrical signal, and a second switch arranged between the second conversion element and the detection signal line.

23 Claims, 23 Drawing Sheets

(51) Int. Cl.
  *A61B 6/00* (2006.01)
  *H01L 27/146* (2006.01)
  *H04N 5/32* (2006.01)

(52) U.S. Cl.
  CPC .. *H01L 27/14658* (2013.01); *H01L 27/14663* (2013.01); *H04N 5/32* (2013.01)

(58) Field of Classification Search
  CPC ......... G01T 1/243; G01T 1/245; G01T 1/247; G01T 1/362; A61B 6/4208
  USPC .......................................... 378/91, 98.8, 164
  See application file for complete search history.

(56) References Cited

U.S. PATENT DOCUMENTS

| | | | |
|---|---|---|---|
| 7,386,089 B2 | 6/2008 | Endo et al. | 378/5 |
| 7,408,167 B2 | 8/2008 | Kameshima et al. | 250/370.09 |
| 7,421,063 B2 | 9/2008 | Takenaka et al. | 378/116 |
| 7,435,968 B2 | 10/2008 | Watanage et al. | 250/370.14 |
| 7,470,908 B2 | 12/2008 | Ishii et al. | 250/370.08 |
| 7,488,948 B2 | 2/2009 | Ishii et al. | 250/370.11 |
| 7,514,663 B2 | 4/2009 | Yagi et al. | 250/208.1 |
| 7,557,355 B2 | 7/2009 | Mochizuki et al. | 250/370.09 |
| 7,629,564 B2 | 12/2009 | Mochizuki et al. | 250/208.1 |
| 7,645,976 B2 | 1/2010 | Watanabe et al. | 250/208.1 |
| 7,645,995 B2 | 1/2010 | Yagi et al. | 250/370.09 |
| 7,718,973 B2 | 5/2010 | Endo et al. | 250/370.08 |
| 7,732,776 B2 | 6/2010 | Takenaka et al. | 250/369 |
| 7,812,313 B2 | 10/2010 | Mochizuki et al. | 250/370.09 |
| 7,839,977 B2 | 11/2010 | Kameshima et al. | 378/116 |
| 7,869,568 B2 | 1/2011 | Yokoyama et al. | 378/98.8 |
| 7,897,930 B2 | 3/2011 | Mochizuki et al. | 250/370.09 |
| 7,932,946 B2 | 4/2011 | Ishii et al. | 348/294 |
| 8,072,514 B2 | 12/2011 | Takenaka et al. | 348/246 |
| 8,247,779 B2 | 8/2012 | Kameshima et al. | 250/370.09 |
| 8,368,027 B2 | 2/2013 | Ishii et al. | 250/370.08 |
| 8,680,472 B2 | 3/2014 | Mochizuki et al. | 250/370.09 |
| 8,878,972 B2 | 11/2014 | Wayama et al. | 348/294 |
| 2003/0213914 A1* | 11/2003 | Kobayashi | G01T 1/2018 250/370.09 |
| 2010/0148080 A1 | 6/2010 | Endo et al. | 250/370.08 |
| 2010/0294942 A1 | 11/2010 | Mochizuki et al. | 250/366 |
| 2011/0095169 A1* | 4/2011 | Takenaka | H04N 5/3658 250/208.1 |
| 2011/0180717 A1 | 7/2011 | Okada | 250/370.08 |
| 2012/0001079 A1 | 1/2012 | Okada | 250/366 |
| 2013/0162833 A1 | 6/2013 | Wayama et al. | 348/162 |
| 2013/0202086 A1* | 8/2013 | Tsuji | G01T 1/026 378/62 |
| 2013/0342514 A1 | 12/2013 | Yokoyama et al. | 345/204 |
| 2015/0182182 A1 | 7/2015 | Tajima | 378/189 |

FOREIGN PATENT DOCUMENTS

| | | |
|---|---|---|
| EP | 1746442 | 1/2007 |
| JP | 2011-174908 | 9/2011 |
| JP | 2012-015913 | 1/2012 |
| WO | WO 01/76228 A | 10/2001 |
| WO | WO 2014/045835 A | 3/2014 |

OTHER PUBLICATIONS

EESR dated Jul. 24, 2015 in counterpart EPA 15163963.0 (in English).
EPO Office Action dated Apr. 11, 2017 in counterpart EPA 15163963.0 (in English).
Office Action issued on Oct. 9, 2017 in P.R. China counterpart 201510214405.X, with translation.

* cited by examiner

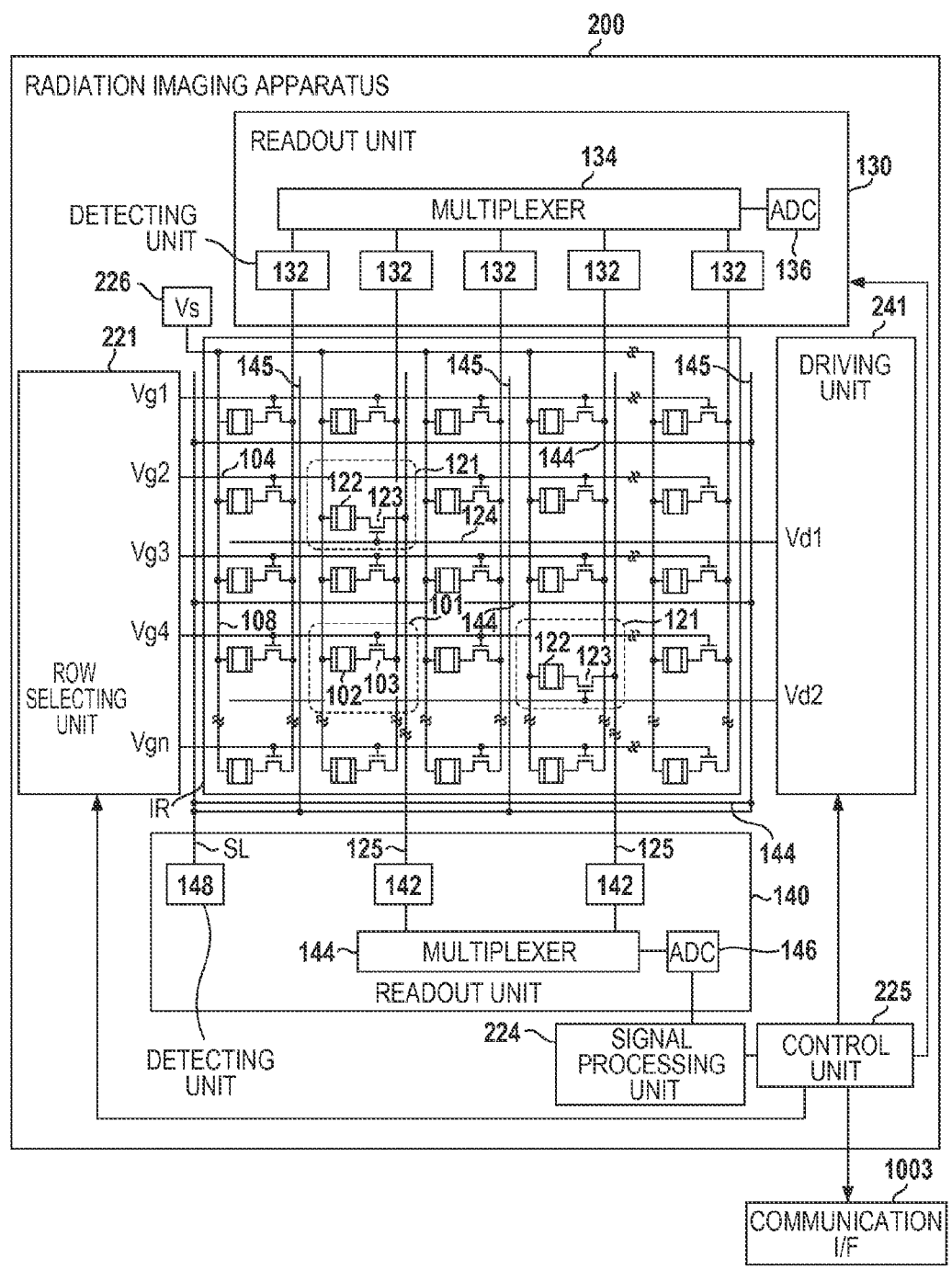
F I G. 10

F I G. 18
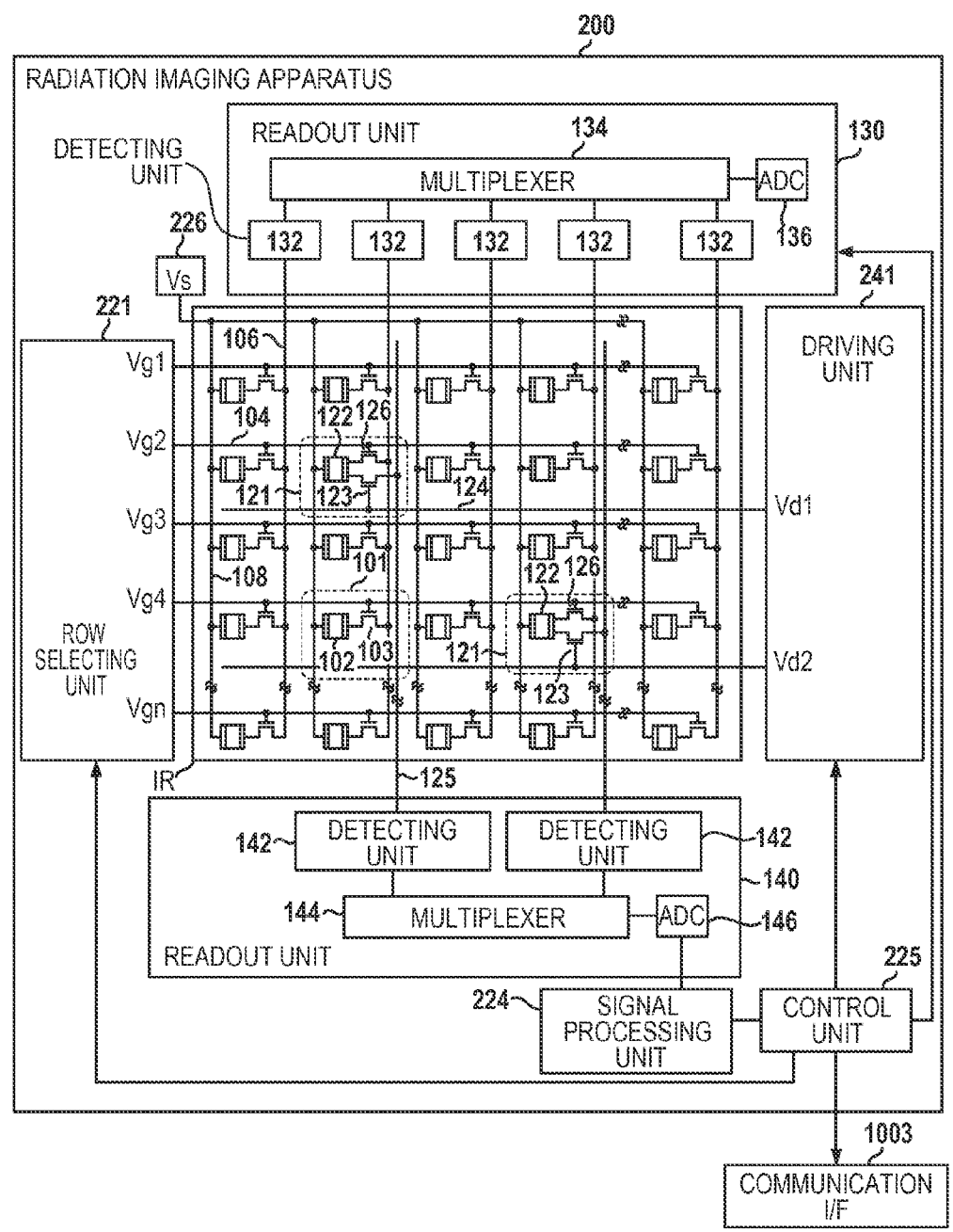

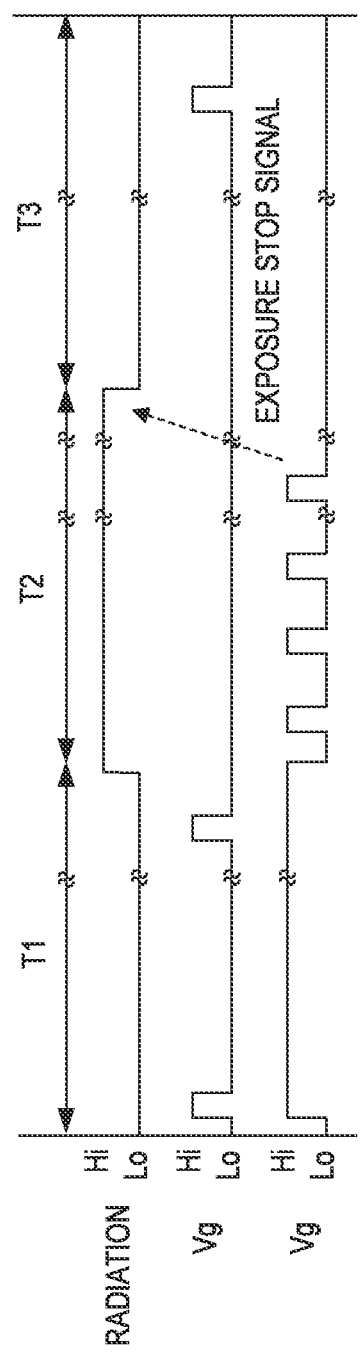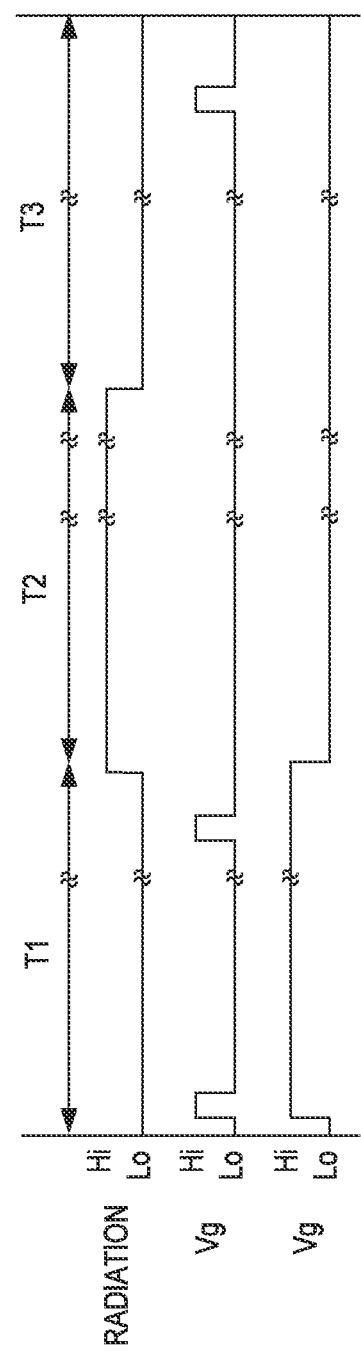

RADIATION IMAGING APPARATUS AND RADIATION IMAGING SYSTEM

BACKGROUND OF THE INVENTION

Field of the Invention

The present invention relates to a radiation imaging apparatus and a radiation imaging system.

Description of the Related Art

Radiation imaging apparatuses having matrix substrates with pixel arrays in which switches such as TFTs (thin film transistors) and conversion elements such as photoelectric conversion elements are combined have been put to practical use as radiation imaging apparatuses used for medical imaging diagnosis and non-destructive examination by means of radiation such as X-rays.

In recent years, consideration has been given to increasing the functions of radiation imaging apparatuses. One way of increasing the functions that has been considered is including a function of monitoring the irradiation of radiation. For example, this function enables detection of the timing at which irradiation of radiation from a radiation source starts, detection of the timing at which the irradiation of the radiation is to be stopped, and detection of the irradiation amount or the integrated irradiation amount of the radiation.

Japanese Patent Laid-Open No. 2012-15913 discloses a radiation detection apparatus that includes pixels for obtaining a radiation image and pixels for detecting radiation. With the radiation detecting apparatus disclosed in Japanese Patent Laid-Open No. 2012-15913, signals of pixels for obtaining a radiation image and signals of pixels for detecting radiation are read out from the same signal line via a switch.

Japanese Patent Laid-Open No. 2011-174908 also discloses a radiation detection apparatus that includes pixels for obtaining a radiation image and pixels for detecting radiation. With the radiation detection apparatus disclosed in Japanese Patent Laid-Open No. 2011-174908, a dedicated signal line for detecting radiation is provided, and photoelectric conversion elements of pixels for detecting radiation are directly connected to the dedicated signal line.

With the radiation detecting apparatus disclosed in Japanese Patent Laid-Open No. 2012-15913, signals of pixels for obtaining a radiation image and signals of pixels for detecting radiation are read out via the same signal line. Accordingly, the signal line has a large parasitic capacitance, and it is difficult to read out the signals at a high speed from the pixels for detecting the radiation. For this reason, it is difficult to accurately perform control of the end of exposure and the like.

With the radiation detection apparatus disclosed in Japanese Patent Laid-Open No. 2011-174908, the number of dedicated signal lines needs to be the same as the number of detection areas in order to individually detect the irradiation of radiation on any detection area. In particular, if multiple pixels for detecting radiation are arranged in one column, the same number of dedicated signal lines as the pixels need to be arranged in that column. This causes an increase in the array pitch of the pixels or a reduction in the sensitivity of the pixels.

SUMMARY OF THE INVENTION

The present invention provides a technique that is advantageous for monitoring the irradiation of radiation with high responsiveness while suppressing an increase in the array pitch of pixels or a reduction in the sensitivity of the pixels.

A first aspect of the present invention provides a radiation imaging apparatus having a plurality of pixels arrayed in an imaging area so as to form a plurality of rows and a plurality of columns, the plurality of pixels including a plurality of imaging pixels for obtaining a radiation image and a detecting pixel for detecting radiation, the radiation imaging apparatus comprising: a plurality of column signal lines respectively corresponding to the plurality of columns; and a detection signal line corresponding to the detecting pixel, wherein each of the imaging pixels includes a first conversion element configured to convert radiation into an electrical signal, and a first switch arranged between the first conversion element and a corresponding column signal line among the plurality of column signal lines, and the detecting pixel includes a second conversion element configured to convert radiation into an electrical signal, and a second switch arranged between the second conversion element and the detection signal line.

Further features of the present invention will become apparent from the following description of exemplary embodiments with reference to the attached drawings.

BRIEF DESCRIPTION OF THE DRAWINGS

FIG. 10 is a diagram showing a configuration of the radiation imaging apparatus according to the third embodiment of the present invention.

FIG. 18 is a diagram showing a configuration of the radiation imaging apparatus according to a seventh embodiment of the present invention.

FIGS. 19A and 19B are diagrams showing operations performed by the radiation imaging apparatus according to the seventh embodiment of the present invention.

DESCRIPTION OF THE EMBODIMENTS

Hereinafter, the present invention will be described via exemplary embodiments thereof, with reference to the accompanying drawings.

Figure 1:
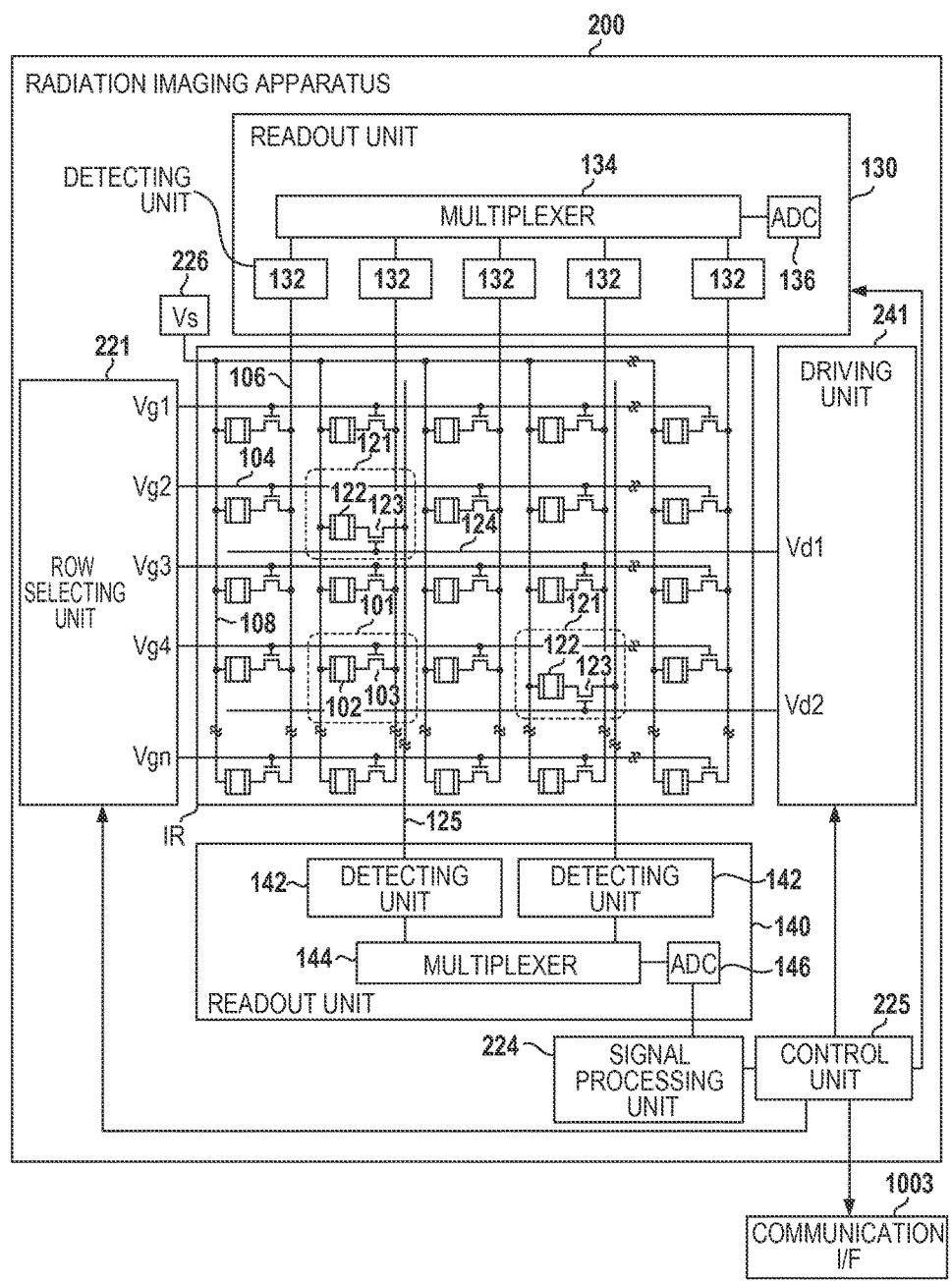
FIG. 1 is a diagram showing a configuration of a radiation imaging apparatus according to a first embodiment of the present invention.
Figure 6A:
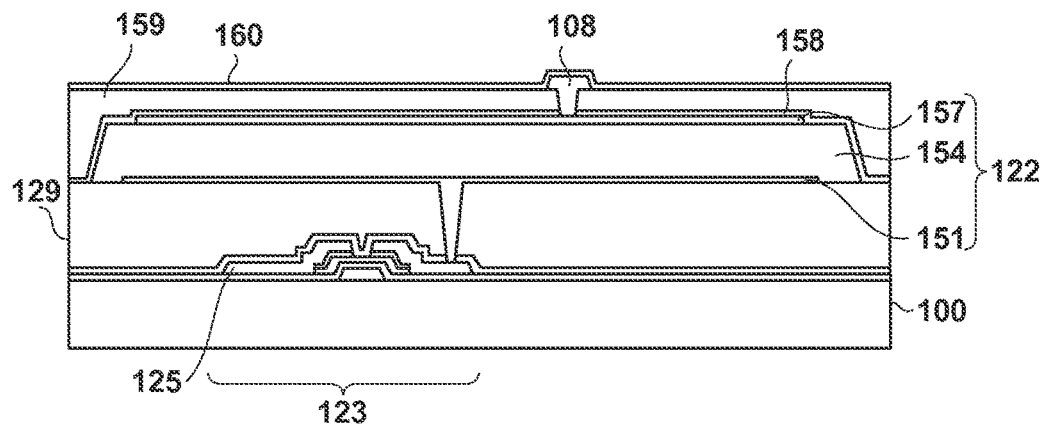
FIG. 6A is a cross-sectional view taken along line A-A' in FIG. 5.
Figure 6B:
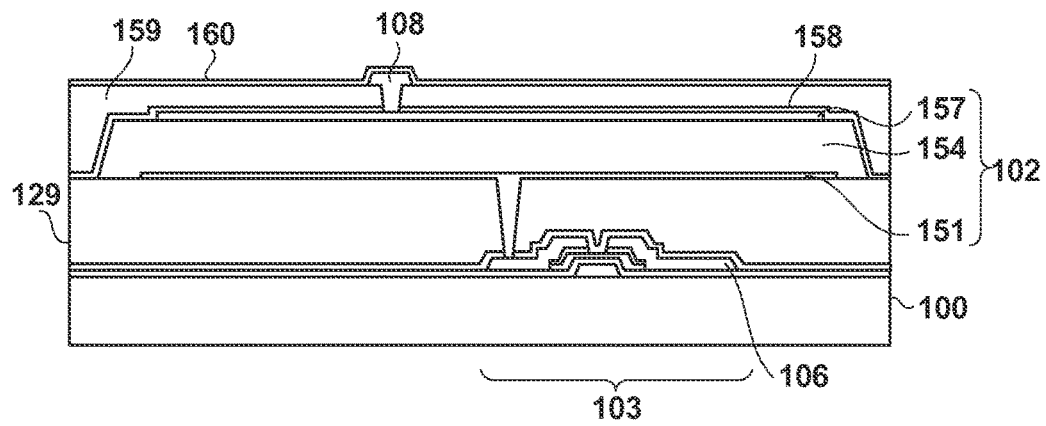
FIG. 6B is a cross-sectional view taken along line B-B' in FIG. 5.

FIG. 1 shows a configuration of a radiation imaging apparatus 200 according to a first embodiment of the present invention. The radiation imaging apparatus 200 has multiple pixels that are arrayed in an imaging area IR so as to form multiple rows and multiple columns. The multiple pixels include multiple imaging pixels 101 for obtaining a radiation image, and a detecting pixel 121 for detecting radiation. The multiple pixels can be arrayed on a support substrate 100 as shown in FIGS. 6A and 6B. The imaging pixels 101 each include a first conversion element 102 that converts radiation into an electrical signal, and a first switch 103 that is arranged between a column signal line 106 and the first conversion element 102. The detecting pixels 121 each include a second conversion element 122 that converts radiation into an electrical signal, and a second switch 123 that is arranged between a detection signal line 125 and the second conversion element 122.

The first conversion element 102 and the second conversion element 122 can be formed by a scintillator that converts radiation into light and a photoelectric conversion element that converts the light into an electrical signal. The scintillator can usually be formed in a sheet shape so as to cover the imaging area IR, and it can be shared by multiple pixels. Alternatively, the first conversion element 102 and the second conversion element 122 can be formed using a conversion element that converts radiation directly into light.

The first switch 103 and the second switch 123 can, for example, include a thin film transistor (TFT) in which an active area is formed by a semiconductor such as amorphous silicon or polycrystalline silicon (preferably polycrystalline silicon).

The radiation imaging apparatus 200 has multiple column signal lines 106 and multiple driving lines 104. The multiple column signal lines 106 correspond to the multiple columns in the imaging area IR. That is to say, one column signal line 106 corresponds to one of the multiple columns in the imaging area IR. The multiple driving lines 104 correspond to the multiple rows in the imaging area IR. That is to say, one driving line 104 corresponds to one of the multiple rows in the imaging area IR. The driving lines 104 are driven by a row selecting unit 221.

A first electrode of the first conversion element 102 is connected to a first main electrode of the first switch 103, and a second electrode of the first conversion element 102 is connected to a bias line 108. Here, one bias line 108 extends in the column direction and is connected in common to the second electrodes of multiple conversion elements 102 that are arranged in the column direction. The bias line 108 receives a bias voltage Vs from a power source circuit 226. Second main electrodes of the first switches 103 of multiple imaging pixels 101 that form one column are connected to, among the multiple column signal lines 106, the column signal line 106 corresponding to that column. Control electrodes of the first switches 103 of multiple imaging pixels 101 that form one row are connected to one driving line 104.

The multiple column signal lines 106 are connected to a readout unit 130. Here, the readout unit 130 can include multiple detecting units 132, a multiplexer 134, and an analog-digital converter (referred to below as "AD converter") 136. The column signal lines 106 are each connected to a corresponding detecting unit 132 among the multiple detecting units 132 of the readout unit 130. Here, one column signal line 106 corresponds to one detecting unit 132. The detecting units 132 each include a differential amplifier, for example. The multiplexer 134 selects the multiple detecting units 132 in a predetermined order and supplies the signal from the selected detecting unit 132 to the AD converter 136. The AD converter 136 converts the supplied signal into a digital signal and outputs it.

A first electrode of the second conversion element 122 is connected to a first main electrode of the second switch 123, and a second electrode of the second conversion element 122 is connected to the bias line 108. The second main electrode of the second switch 123 is electrically connected to the detection signal line 125. The control electrode of the second switch 123 is electrically connected to the driving line 124. The radiation imaging apparatus 200 can have multiple detection signal lines 125. One or more detecting pixels 121 can be connected to one detection signal line 125. The driving line 124 is driven by the driving unit 241. One or more detecting pixels 121 can be connected to one driving line 124.

The detection signal line 125 is connected to a readout unit 140. Here, the readout unit 140 can include multiple detecting units 142, a multiplexer 144, and an AD converter 146. The detection signal lines 125 can each be connected to a corresponding detecting unit 142 among the multiple detecting units 142 of the readout unit 140. Here, one detection signal line 125 corresponds to one detecting unit 142. A detecting unit 142 includes a differential amplifier, for example. The multiplexer 144 selects the multiple detecting units 142 in a predetermined order and supplies the signal from the selected detecting unit 142 to the AD converter 146. The AD converter 146 converts the supplied signal into a digital signal and outputs it.

The output of the readout unit 140 (AD converter 146) is supplied to a signal processing unit 224 and is processed by the signal processing unit 224. Based on the output of the readout unit 140 (AD converter 146), the signal processing unit 224 outputs information indicating irradiation of radiation on the radiation imaging apparatus 200. Specifically, the signal processing unit 224 detects irradiation of radiation on the radiation imaging apparatus 200, and calculates the irradiation amount and/or the integrated irradiation amount of the radiation. Based on the information from the signal processing unit 224, the control unit 225 controls the row selecting unit 221, the driving unit 241, and the readout unit 130. For example, based on the information from the signal processing unit 224, the control unit 225 controls the start and end of exposure (accumulation of charge corresponding to the emitted radiation in the imaging pixels 101). The signal processing unit 224 and the control unit 225 can be implemented by, for example, an application specific integrated circuit (ASIC)), or a computer that reads out and executes computer executable instructions (programs) recorded on a storage medium.

Figure 2:
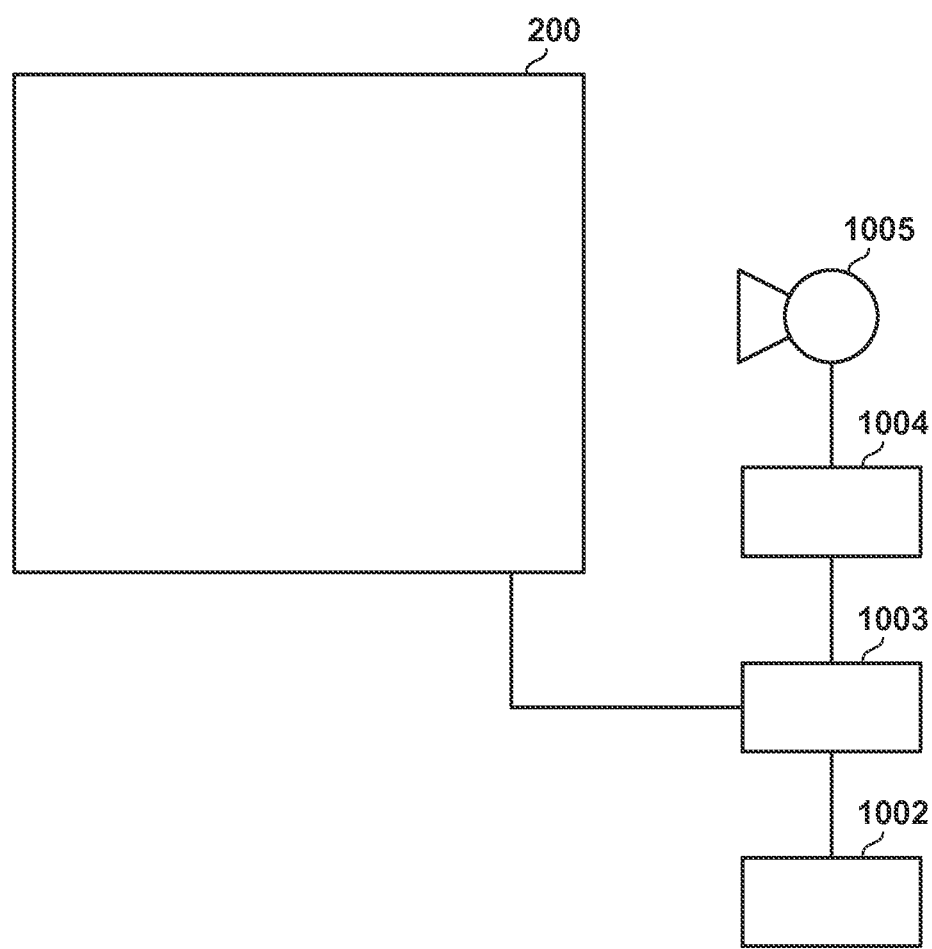
FIG. 2 is a diagram showing an example of a configuration of a radiation imaging system that includes a radiation imaging apparatus.

A configuration of a radiation imaging system including the radiation imaging apparatus 200 is illustrated in FIG. 2. In addition to the radiation imaging apparatus 200, the radiation imaging system includes a controller 1002, an interface 1003, a radiation source interface 1004, and a radiation source 1005.

The controller 1002 can receive input of information such as a radiation dose A, an irradiation time B (ms), a tube current C (mA), a tube voltage D (kV), and a radiation detection area (ROI) which is an area in which radiation is to be monitored. The input information is sent to the radiation imaging apparatus 200 via the interface 1003. If an exposure switch attached to the radiation source 1005 is operated, radiation is radiated from the radiation source 1005. For example, using the detecting pixels 121 arranged in the radiation detection area (ROI), the radiation imaging apparatus 200 performs a detection operation for detecting irradiation of radiation, and detects the timing of the start of irradiation of radiation. Next, when the integrated value of the signals read out from the detecting pixels 121 arranged in the radiation detection area (ROI) reaches a radiation dose A', for example, the control unit 225 of the radiation imaging apparatus 200 sends an exposure stop signal to the radiation source interface 1004 via the interface 1003. In response to this, the radiation source interface 1004 causes the radiation source 1005 to stop radiating radiation. Here, the radiation dose A' can be set by the control unit 225 based on the radiation dose A, the radiation irradiation intensity, communication delay between units, processing delay, and the like. When the time for emitting radiation reaches an irradiation time B, the radiation source 1005 stops the irradiation of radiation regardless of whether or not there is an exposure stop signal.

In the first embodiment, image information cannot be read out at locations at which the detecting pixels 121 exist, but image information for the locations at which the detecting pixels 121 exist can be obtained by performing interpolation processing using the output of the imaging pixels 101 in the periphery of the detecting pixels 121.

Figure 3:
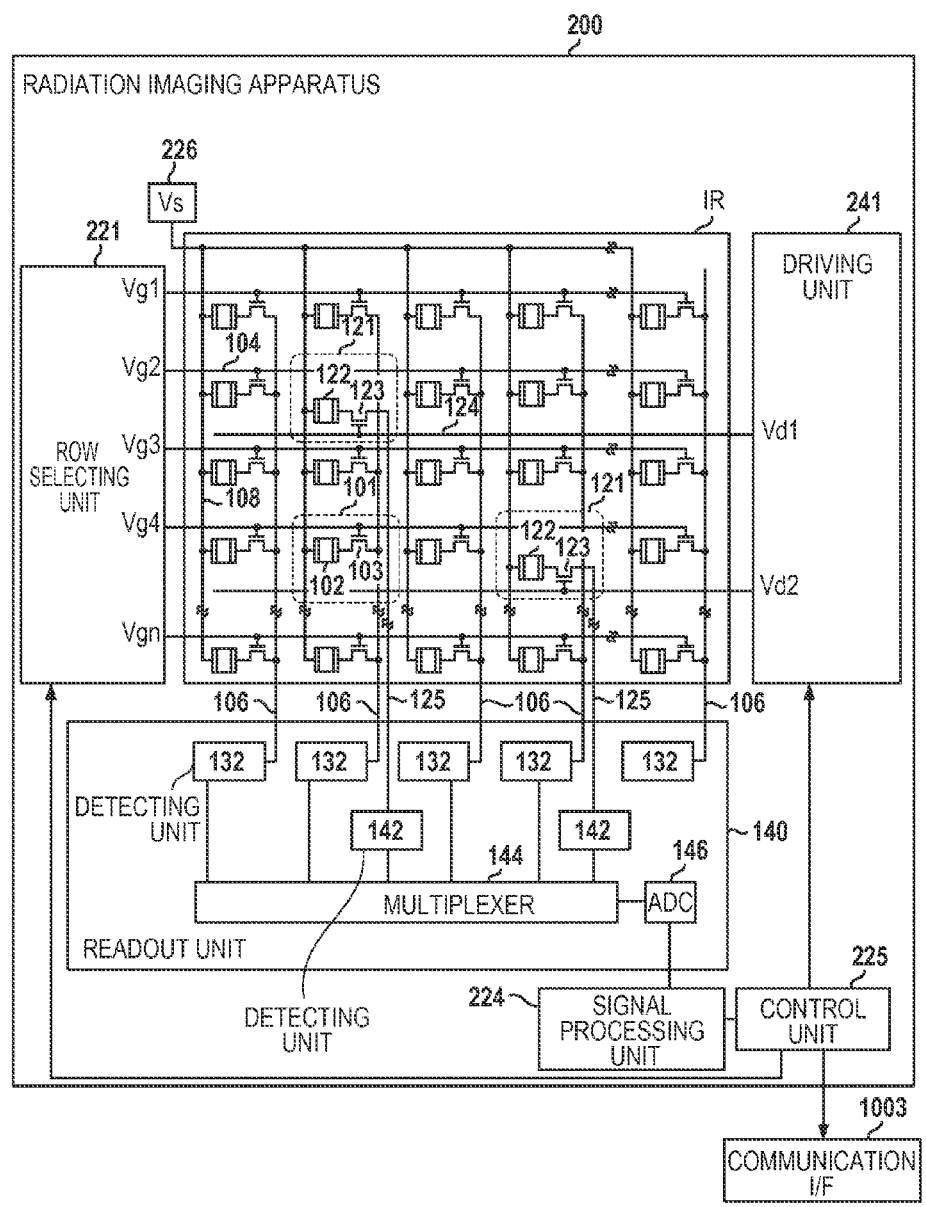
FIG. 3 is a diagram showing a configuration of a modified example of the radiation imaging apparatus according to the first embodiment of the present invention.

In the configuration example shown in FIG. 1, the signals from the imaging pixels 101 and the signals from the detecting pixels 121 are read out by separate readout units 130 and 140, but as illustrated in FIG. 3, they may be read out by a common readout unit 140.

Figure 4:
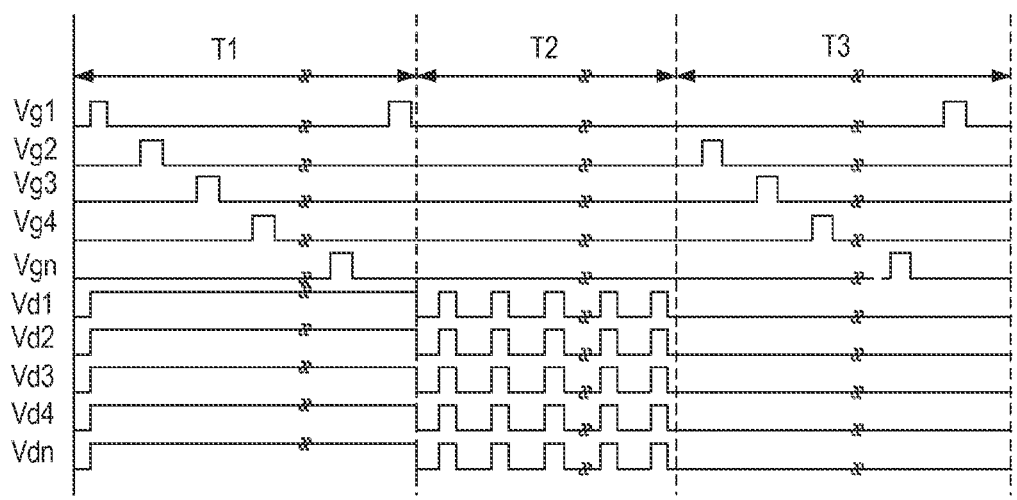
FIG. 4 is a diagram showing operations performed by the radiation imaging apparatus according to the first embodiment of the present invention.

FIG. 4 illustrates operations of the radiation imaging apparatus 200 according to the first embodiment of the present invention. In the description below, let Vg1 to Vgn be signals that are applied to the driving line 104 that drives the imaging pixels 101, and let Vd1 to Vdn be signals that are applied to the driving line 124 that drives the detecting pixels 121. The first switch 103 and the second switch 123 are turned on when the signal supplied to the gate is at a high level, and are turned off when the signal supplied to the gate is at a low level.

Period T1 is a period of waiting for the start of irradiation of radiation. Specifically, period T1 is from when the power source of the radiation imaging apparatus 200 is switched on and imaging of a radiation image becomes possible to when the exposure switch of the radiation source 1005 is operated and the irradiation of radiation is detected.

In period T1, Vd1 to Vdn are fixed at the high level, and the second switches 123 of the detecting pixels 121 are fixed in the on state. The signals read out by the readout unit 140 from the detecting pixels 121 are processed by the signal processing unit 224, and thus the start of irradiation of radiation is detected. When the start of irradiation of radiation is detected, period T2 is entered. In period T1, in order to remove dark currents generated in the conversion elements 102, it is desirable that the conversion elements 102 are periodically reset to a fixed potential. In this example, the voltages Vg1 to Vgn of the driving lines 104 are switched to the high level in sequence, and the conversion elements 102 are electrically connected to the column signal lines 106, which are fixed at a constant voltage. This prevents charges resulting from the dark currents from being accumulated over a long time in the conversion elements 102. The length of period T1 varies significantly depending on the imaging method, imaging conditions, and the like, and for example, can be several seconds to several minutes.

Period T2 is a period during which radiation is emitted. For example, period T2 is a period from when the start of irradiation of radiation is detected to when the exposure amount of the radiation reaches an optimal radiation dose. It can also be said that period T2 is a period during which the irradiation amount of radiation is monitored. In period T2, Vd1 to Vdn are intermittently switched to the high level, and the second switches 123 of the detecting pixels 121 are intermittently switched to the on state.

The signals read out by the readout unit 140 from the detecting pixels 121 are processed by the signal processing unit 224, and thus the radiation dose is detected. In period T2, the signals Vg1 to Vgn that are applied to the driving lines 104 are switched to the low level. Accordingly, the generated charges are accumulated in the first conversion elements 102 of the imaging pixels 101. The length of period T2 varies significantly depending on the imaging method, imaging conditions, and the like, and for example, can be 1 millisecond to around several hundred milliseconds.

When the integrated value of the signals read out from the detecting pixels 121 arranged in the radiation detection area (ROI) reaches the radiation dose A', the control unit 225 causes the operation of the radiation imaging apparatus 200 to enter period T3. Also, at this time, the control unit 225 sends the exposure stop signal to the radiation source interface 1004 via the interface 1003.

Period T3 is a period during which signals accumulated in the imaging pixels 101 due to the radiation are read out after the irradiation of radiation has ended. In period T3, Vd1 to Vdn are switched to the low level. In period T3, in order to prevent the detection signal line 125 from floating, it is preferable that the detection signal line 125 is connected to a fixed potential.

In period T3, Vg1 to Vgn are switched to the high level in sequence in order to scan multiple rows. The signals accumulated in the imaging pixels 101 are read out by the readout unit 140. In this example, the row to which the high level is first applied is determined according to the row to which the high level was last applied in period T1, such that the accumulation times for the imaging pixels 101 are the same. In FIG. 4, the row to which the high level was last applied in period T1 is the row corresponding to Vg1, and therefore in period T3, the high level is applied in sequence starting from the row corresponding to Vg2.

In the first embodiment, the second conversion elements 122, which are conversion elements of the detecting pixels 121, are connected to the detection signal lines 125, which are signal lines provided separately from the column signal lines 106 for reading out the signals from the imaging pixels 101, and therefore the imaging pixels 101 are not connected to the detection signal lines 125. Accordingly, it is possible to reduce the parasitic capacitances of the detection signal lines 125, making it possible to monitor the irradiation of radiation with a high responsiveness.

Also, in the first embodiment, by providing the second switches 123, which are switches for the detecting pixels 121, the number of detection signal lines 125 can be reduced and irradiation of radiation can be detected by each of the detecting pixels 121. Here, a configuration in which radiation can be detected by each of the detecting pixels 121, or in each radiation detection area (ROI) that includes at least one detecting pixel 121, contributes to the realization of more suitable radiation dose control and exposure control.

Figure 5:
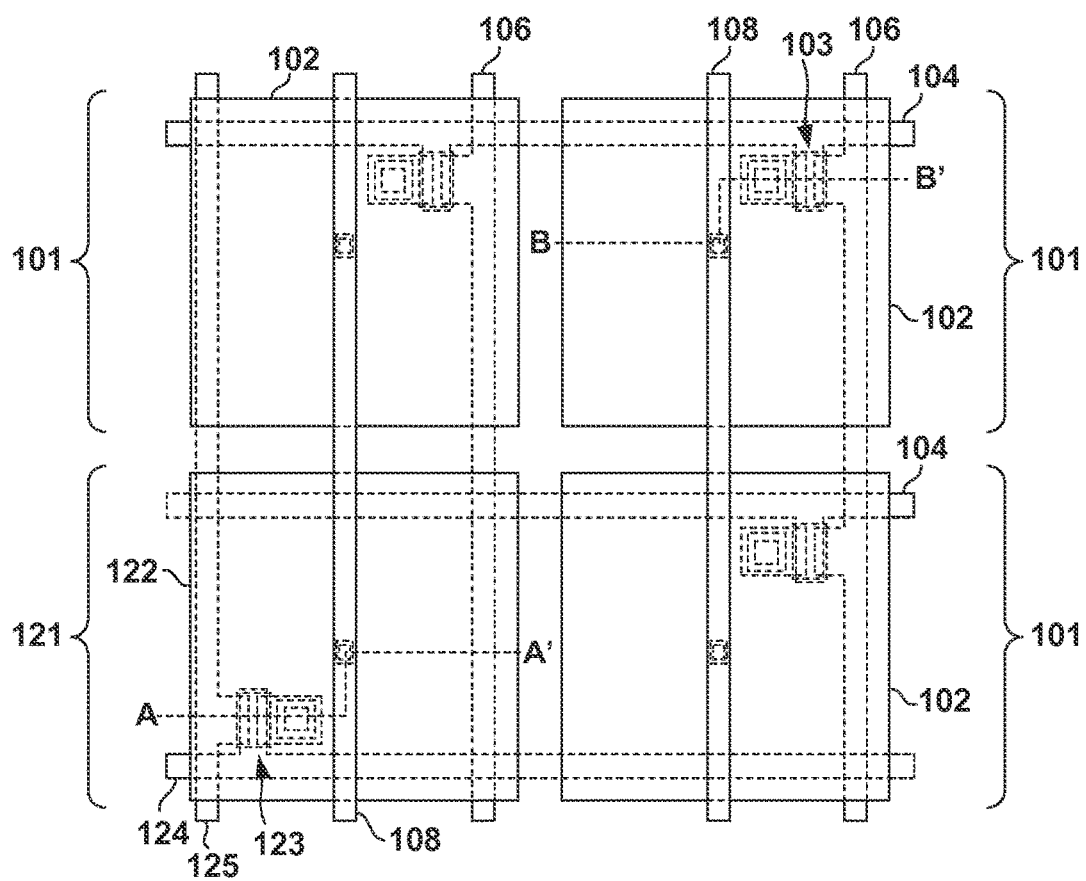
FIG. 5 is a plan view showing a configuration of imaging pixels and a detecting pixel in the radiation imaging apparatus according to the first embodiment of the present invention.

FIG. 5 is a plan view showing a configuration of imaging pixels 101 and a detecting pixel 121 in the radiation imaging apparatus 200 according to the first embodiment of the present invention. Here, the plan view is equivalent to an orthographic projection on a surface parallel to the imaging area IR of the radiation imaging apparatus 200. FIG. 6A is a cross-sectional view taken along line A-A' in FIG. 5, and FIG. 6B is a cross-sectional view taken along line B-B' in FIG. 5.

As illustrated in FIG. 5 and FIG. 6A, the detecting pixel 121 includes the second conversion element 122 and the second switch 123. In this example, radiation is converted into light by a scintillator (not shown), and the second conversion element 122 converts the light into a charge and accumulates it. Note that the second conversion element 122 may be configured to convert the radiation directly into a charge. The second switch 123 includes a TFT (thin film transistor) that outputs an electrical signal corresponding to the charge accumulated in the second conversion element 122. The second conversion element 122 can be a PIN photodiode 154, for example. The second conversion element 122 is connected to the detection signal line 125 via the second switch 123. The second conversion element 122 can be arranged above the second switch 123 arranged on the insulating support substrate 100, which is a glass substrate or the like, with an interlayer insulating layer 129 interposed therebetween. For example, the second conversion element 122 can be configured by the first electrode 151, the PIN photodiode 154, and the second electrode 157.

Above the second conversion element 122, a protective film 158, a second inter-layer insulating layer 159, a bias line 108, and a protective film 160 are arranged in the stated order. A flattening film and a scintillator (not shown) are arranged above the protective film 160. The second electrode 157 is connected to the bias line 108 via a contact hole. ITO, which has a light-transmitting property, is used for the second electrode 157, which is configured to be able to transmit light after it has been converted from radiation by the scintillator (not shown).

As illustrated in FIG. 5 and FIG. 6B, the imaging pixel 101 includes the first conversion element 102 and the first switch 103. In this example, radiation is converted into light by a scintillator (not shown), and similarly to the second conversion element 122, the first conversion element 102 converts the light into a charge and accumulates it. Note that the first conversion element 102 may be configured to convert the radiation directly into a charge. The first switch 103 includes a TFT (thin film transistor) that outputs an electrical signal corresponding to the charge accumulated in the first conversion element 102. The first conversion element 102 can be the PIN photodiode 154, for example. The first conversion element 102 is connected to the column signal line 106 via the first switch 103. The first conversion element 102 can be arranged above the first switch 103 arranged on the insulating support substrate 100, which is a glass substrate or the like, with an interlayer insulating layer 129 interposed therebetween. For example, the first conversion element 102 can be configured by the first electrode 151, the PIN photodiode 154, and the second electrode 157. The first conversion element 102 and the second conversion element 122 may be configured by a MIS sensor for example.

Figure 7:
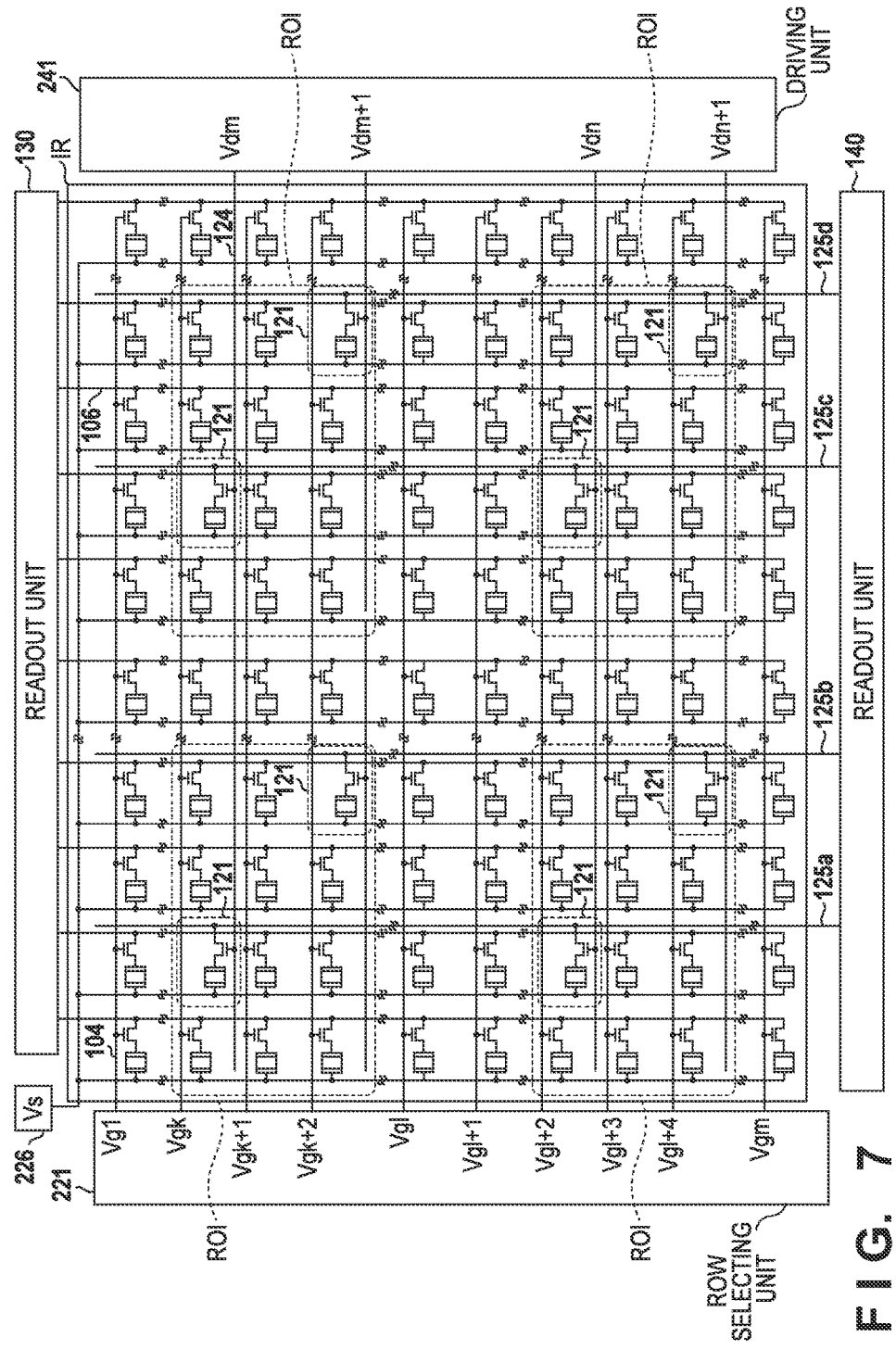
FIG. 7 is a diagram showing an example of an arrangement of detecting pixels.

FIG. 7 shows an example of an arrangement of the detecting pixels 121. Note that pixels that are not denoted by a reference numeral are imaging pixels. In the arrangement example shown in FIG. 7, four radiation detection areas ROI are provided. A radiation detection area ROI is formed by 12 pixels, two of which being detecting pixels 121, and the other 10 of which being imaging pixels. Note that this is merely an example, and according to the intended use, it is possible to freely set the arrangement of the detecting pixels 121 and the configuration of the radiation detection area ROI, examples of which include a configuration in which the radiation detection area is a 50×50-pixel area and pixels in a 5×5-pixel area included therein are the detecting pixels 121, and the like.

In the example shown in FIG. 7, one detecting pixel 121 can be designated by selection of one driving line 124 and one detection signal line 125. For example, due to Vdm being switched to the high level, the detecting pixels 121 connected to the detection signal lines 125a and 125c output a signal to the detection signal lines 125a and 125c, and the signals can be read out individually from the detection signal lines 125a and 125c by the readout unit 140. Accordingly, it is possible to individually monitor the outputs of the multiple detecting pixels 121 in the radiation detection areas ROI. In other words, the radiation detection areas ROI can be divided into multiple blocks so as to monitor the emitted radiation dose.

In another example, the multiple detecting pixels 121 in the radiation detection area ROI may be connected to one detection signal line 125.

Figure 8:
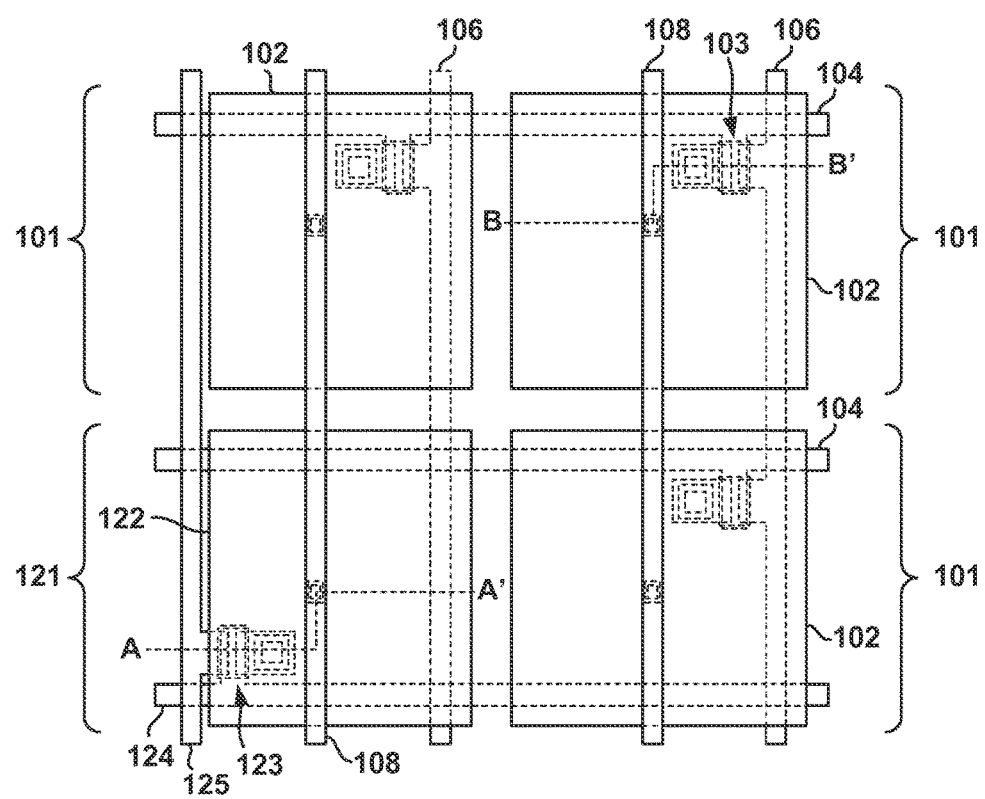
FIG. 8 is a plan view showing a configuration of imaging pixels and a detecting pixel in the radiation imaging apparatus according to a second embodiment of the present invention.

FIG. 8 is a plan view showing a configuration of imaging pixels 101 and a detecting pixel 121 in the radiation imaging apparatus 200 according to a second embodiment of the present invention. Items not mentioned in the second embodiment may be as described in the first embodiment. As illustrated in FIG. 8, in the second embodiment, a configuration is used in which in the orthogonal projection on the surface parallel to the imaging area IR, the detection signal line 125 and the first conversion elements 102 do not overlap and the detection signal line 125 and the second conversion element 122 do not overlap. Accordingly, in the second embodiment, the parasitic capacitance of the detection signal line 125 can be reduced, and according to this, the speed at which the signal is read out from the detecting pixel 121 via the detection signal line 125 can be increased.

Also, in the second embodiment, it is possible to reduce the influence that the potential variations of the first electrodes 151 (see FIGS. 6A, 6B) of the first conversion elements 102 of the imaging pixels 101 has on the detection signal line 125. Specifically, while the radiation is being emitted, the potential of the first electrode 151 of the first conversion element 102 of the imaging pixel 101 varies due to the accumulation of charge. Accordingly, crosstalk can occur between the detection signal line 125 and the first electrodes 151 of the first conversion elements 102 of the imaging pixels 101 due to the parasitic capacitances therebetween. In view of this, in the second embodiment, a configuration is used in which in the orthographic projection on a surface parallel to the imaging area IR, the detection signal line 125 and the first conversion elements 102 do not overlap and the detection signal line 125 and the second conversion element 122 do not overlap. According to this configuration, the parasitic capacitances between the detection signal line 125 and the first electrodes 151 are reduced, and crosstalk is reduced.

In the second embodiment, the first conversion elements 102 of the imaging pixels 101 in the column in which the detection signal line 125 is arranged may be smaller than the first conversion elements 102 of the imaging pixels 101 in the columns in which no detection signal line 125 is arranged. However, it is possible to reduce the influence that this has by adjusting the gain of the detecting unit 132 of the readout unit 130, or by correcting the image output from the radiation imaging apparatus 200.

Figure 9:
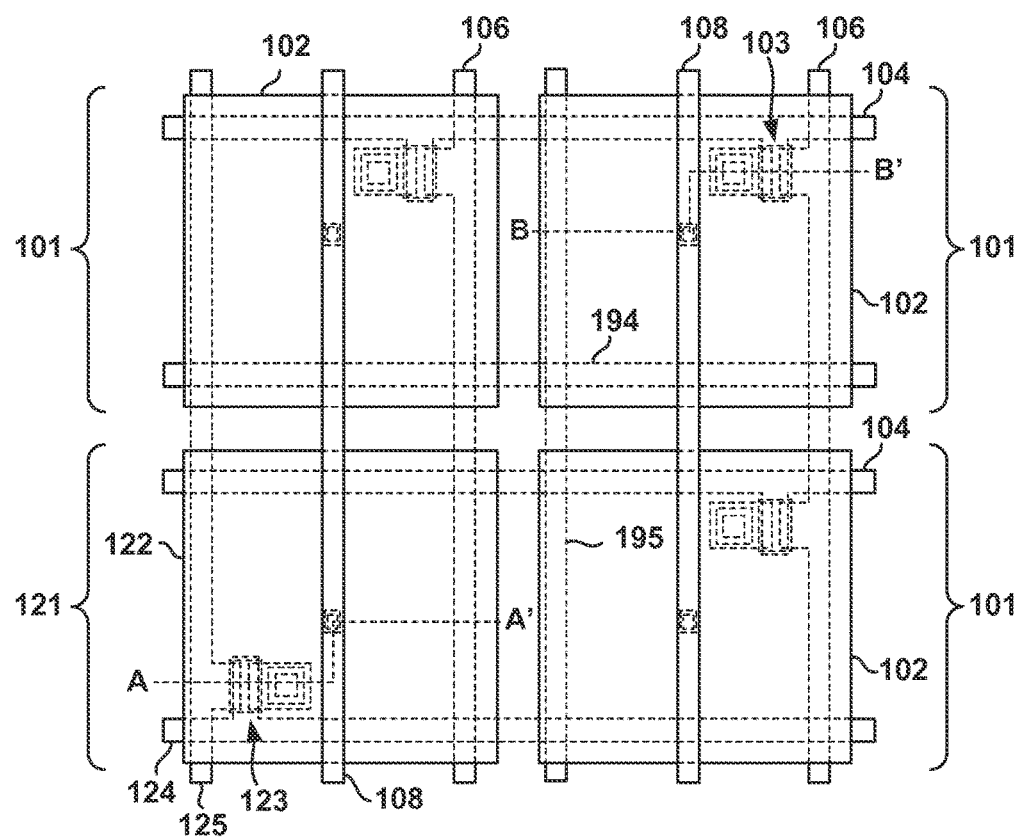
FIG. 9 is a plan view showing a configuration of imaging pixels and a detecting pixel in the radiation imaging apparatus according to a third embodiment of the present invention.

FIG. 9 is a plan view showing a configuration of imaging pixels 101 and a detecting pixel 121 in the radiation imaging apparatus 200 according to a third embodiment of the present invention. Items not mentioned in the third embodiment may be as described in the first or second embodiment. As illustrated in FIG. 9, the radiation imaging apparatus 200 according to the third embodiment has a dummy detection signal line 195 and/or a dummy driving line 194.

The dummy detection signal lines 195 are arranged in the columns in which no detection signal line 125 in the imaging area IR is arranged. That is to say, a portion of the columns included in the imaging area IR are columns in which a column signal line 106 and a detection signal line 125 are arranged. Also, the remaining columns included in the imaging area IR are columns in which a column signal line 106 and a dummy detection signal line 195, which is connected to neither a first switch 103 nor a second switch 123, are arranged.

The dummy driving lines 194 are arranged in rows in which the driving lines 124 for the imaging area IR are not arranged. In other words, a portion of the rows included in the imaging area IR are rows in which the driving lines 104 for driving the first switches 103 and the driving lines 124 for driving the second switches 123 are arranged. Also, the rest of the rows included in the imaging area IR are rows in which the driving lines 104 for driving the first switches 103 and the dummy driving lines 194, which are connected to neither a first switch 103 nor a second switch 123, are arranged.

By providing the dummy detection signal lines 195 and/or the dummy driving lines 194, the capacitances of the first conversion elements 102 can be made uniform in the imaging pixels 101. This makes it possible to reduce artifacts. If the dummy detection signal lines 195 and the dummy driving lines 194 are in a floating state, the potential thereof can vary, and therefore it is preferable that a fixed potential is applied thereto.

The dummy detection signal lines 195 and/or the dummy driving lines 194 may be used to detect the start of irradiation of radiation. This can be achieved by detecting electrical signals that appear in the dummy detection signal lines 195 and/or the dummy driving lines 194, such as a current or a change in voltage. FIG. 10 illustrates a configuration in which the dummy detection signal lines 195 and the dummy driving lines 194 are used to detect the start of irradiation of radiation. In the example shown in FIG. 10, the dummy detection signal lines 195 and the dummy driving lines 194 are connected to each other and are connected to a detecting unit 148 via a common detection line SL. The dummy detection signal lines 195 and the dummy driving lines 194 may be connected to each other in an area outside of the imaging area IR for example.

Parasitic capacitances are formed between the dummy detection signal lines 195 and dummy driving lines 194 and the first electrodes 151 of the first conversion elements 102. Accordingly, the dummy detection signal lines 195, dummy driving lines 194, and the first electrodes 151 of the first conversion elements 102 are capacitively coupled due to the parasitic capacitances, and when irradiation of radiation is started, a current flows in the detection line SL in response to a change in the potential of the first electrode 151. The detecting unit 148 detects the start of the irradiation of radiation based on the current that flows in the detection line SL. By connecting the dummy detection signal lines 195 and the dummy driving lines 194 to the common detection line SL, it is possible to improve the sensitivity with which the start of irradiation of radiation to the radiation imaging apparatus 200 is detected. Also, an operation in which the detecting unit 148 uses the detection line SL to detect the start of radiation, and an operation in which the detecting units 142 use the detecting pixels 121 to detect the start of irradiation of radiation in each radiation detection area ROI may be used in combination. This makes it possible to improve the accuracy of detecting the start of irradiation of radiation.

Figure 11:
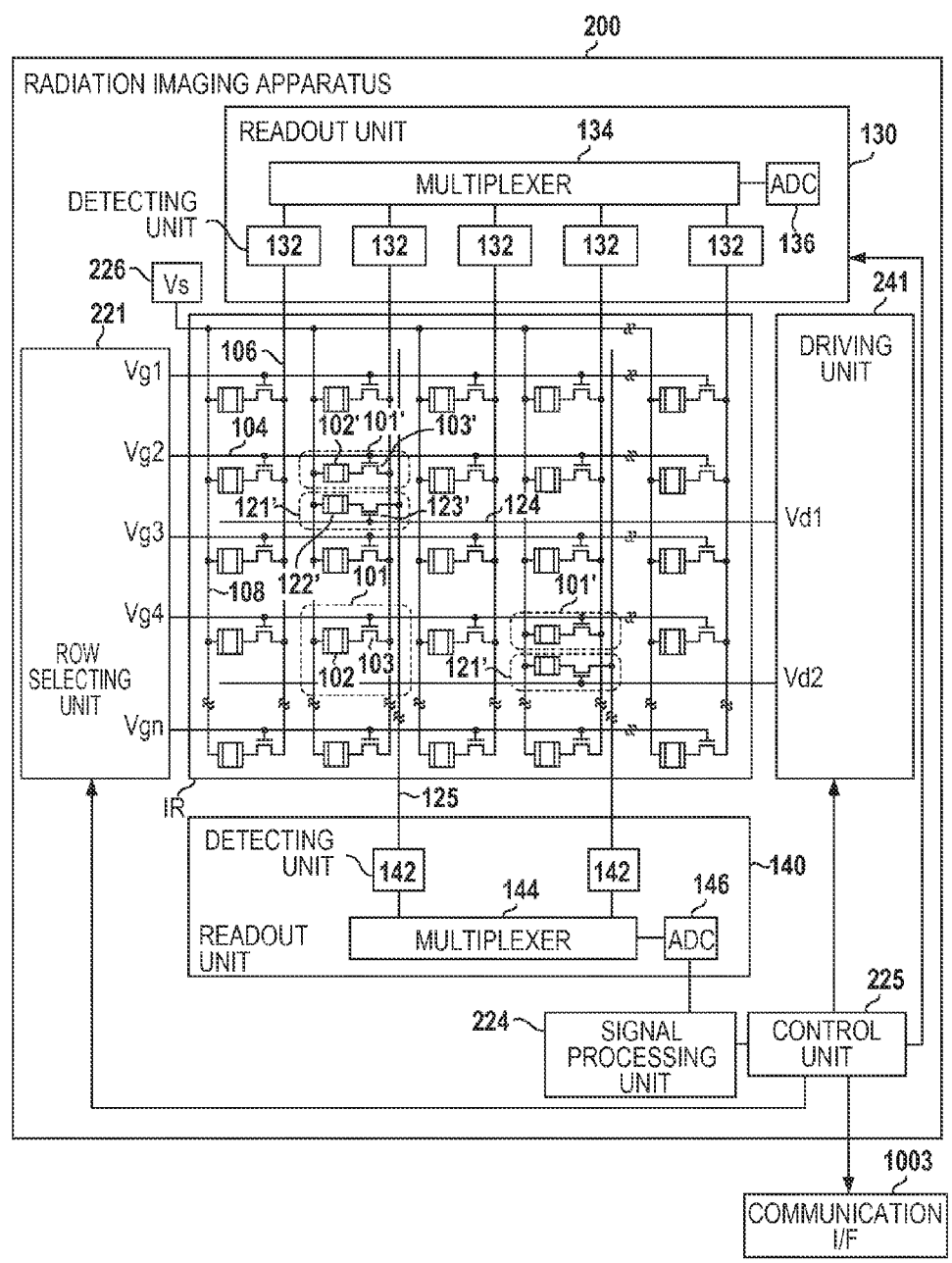
FIG. 11 is a diagram showing a configuration of the radiation imaging apparatus according to a fourth embodiment of the present invention.
Figure 12:
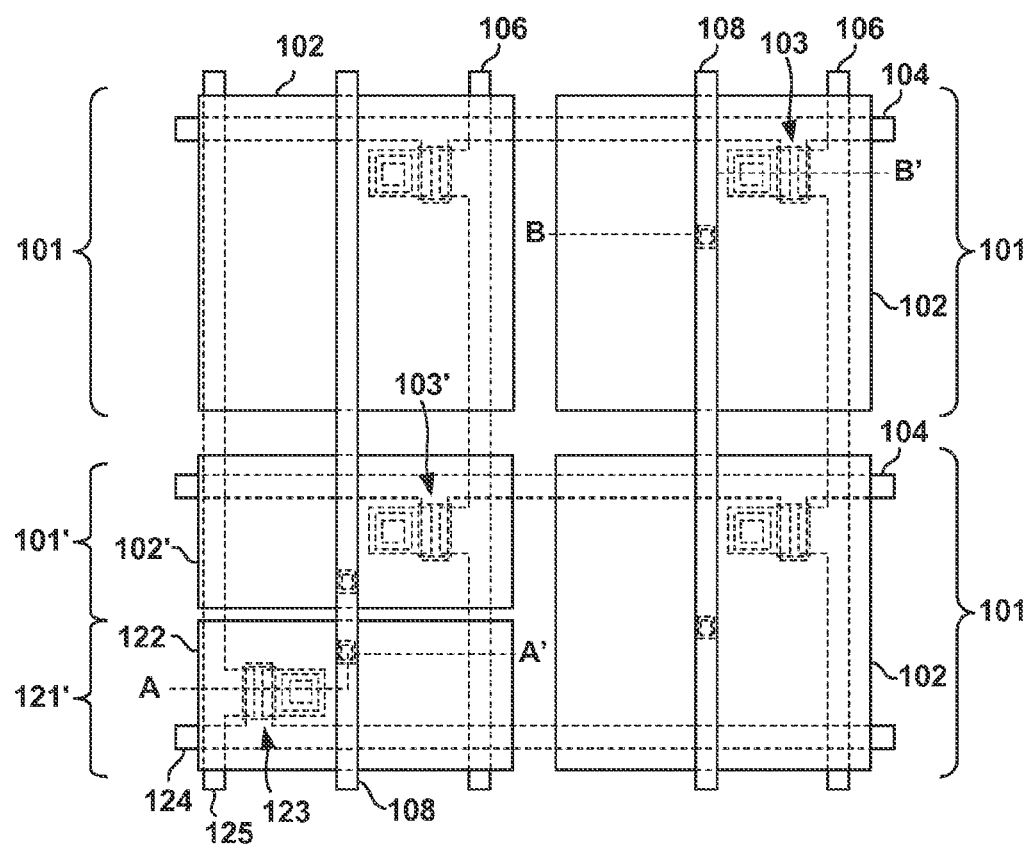
FIG. 12 is a diagram showing a configuration of the radiation imaging apparatus according to the fourth embodiment of the present invention.

FIG. 11 is a diagram showing a configuration of the radiation imaging apparatus 200 according to a fourth embodiment of the present invention. FIG. 12 is a plan view showing a configuration of imaging pixels 101 and a detecting pixel 121 in the radiation imaging apparatus 200 according to the fourth embodiment of the present invention. Elements not mentioned in the fourth embodiment may be as described in the first to third embodiments.

In the fourth embodiment, the imaging area IR is composed of multiple unit areas arrayed so as to form a grid. The multiple unit areas are constituted by unit areas that include only imaging pixels 101 out of the imaging pixels 101 and the detecting pixels 121, and unit areas that include both imaging pixels 101' and detecting pixels 121'. In other words, in the first to third embodiments, there are unit areas that do not include imaging pixels, but in the fourth embodiment, all of the unit areas include the imaging pixels 101 or 101'. The imaging pixels 101' each include a first conversion element 102' and a first switch 103'. The detecting pixels 121' each include a second conversion element 122' and a second switch 123'.

The first conversion elements 102 of the imaging pixels 101 and the first conversion elements 102' of the imaging pixels 101' differ in size, and therefore there is a sensitivity difference between the imaging pixels 101 and the imaging pixels 101'. However, it is possible to reduce the influence that this sensitivity difference has by adjusting the gain of the detecting units 132 of the readout unit 130, or by correcting the image output from the radiation imaging apparatus 200.

Figure 13:
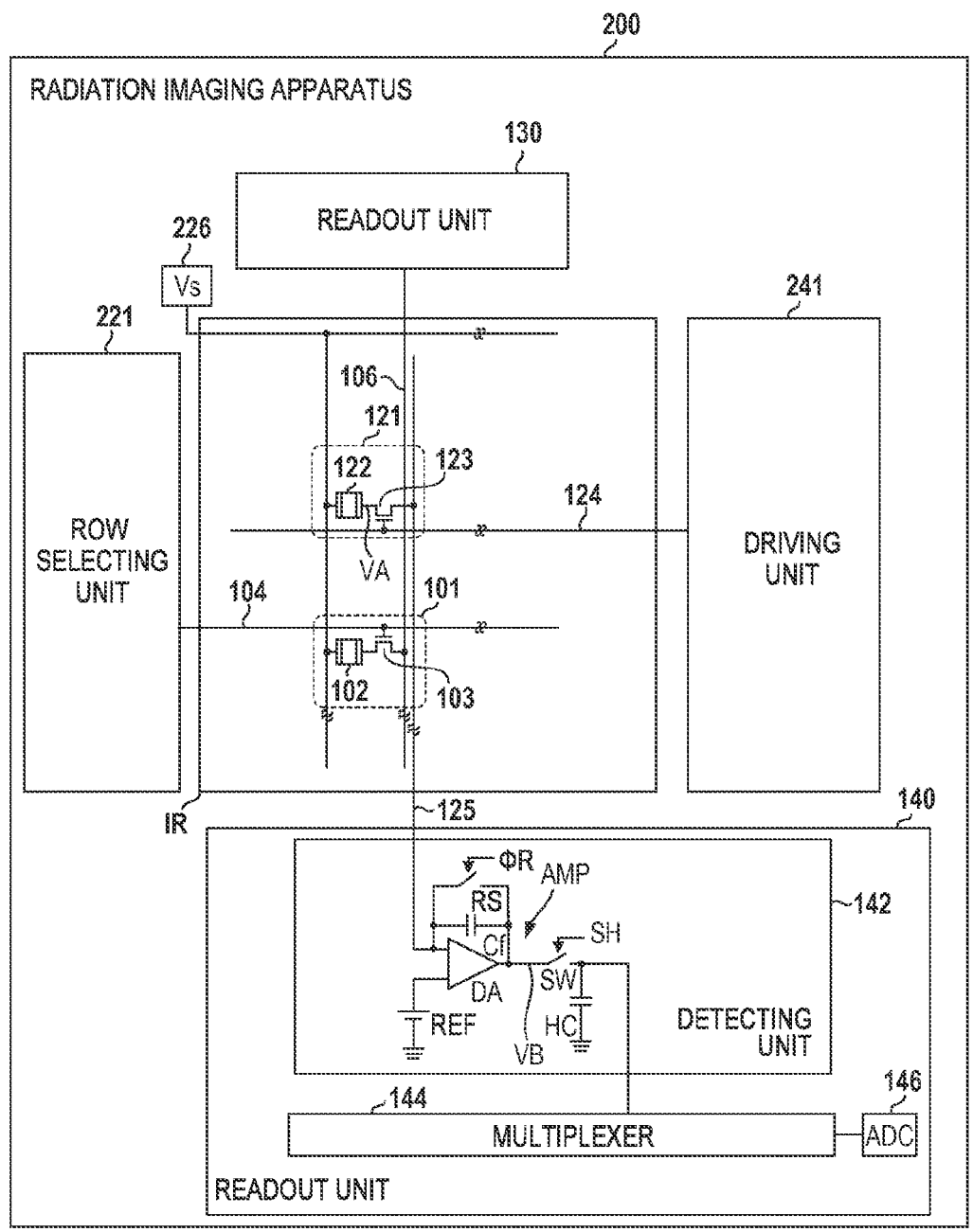
FIG. 13 is a diagram showing a configuration of the radiation imaging apparatus according to a fifth embodiment of the present invention.
Figure 14:
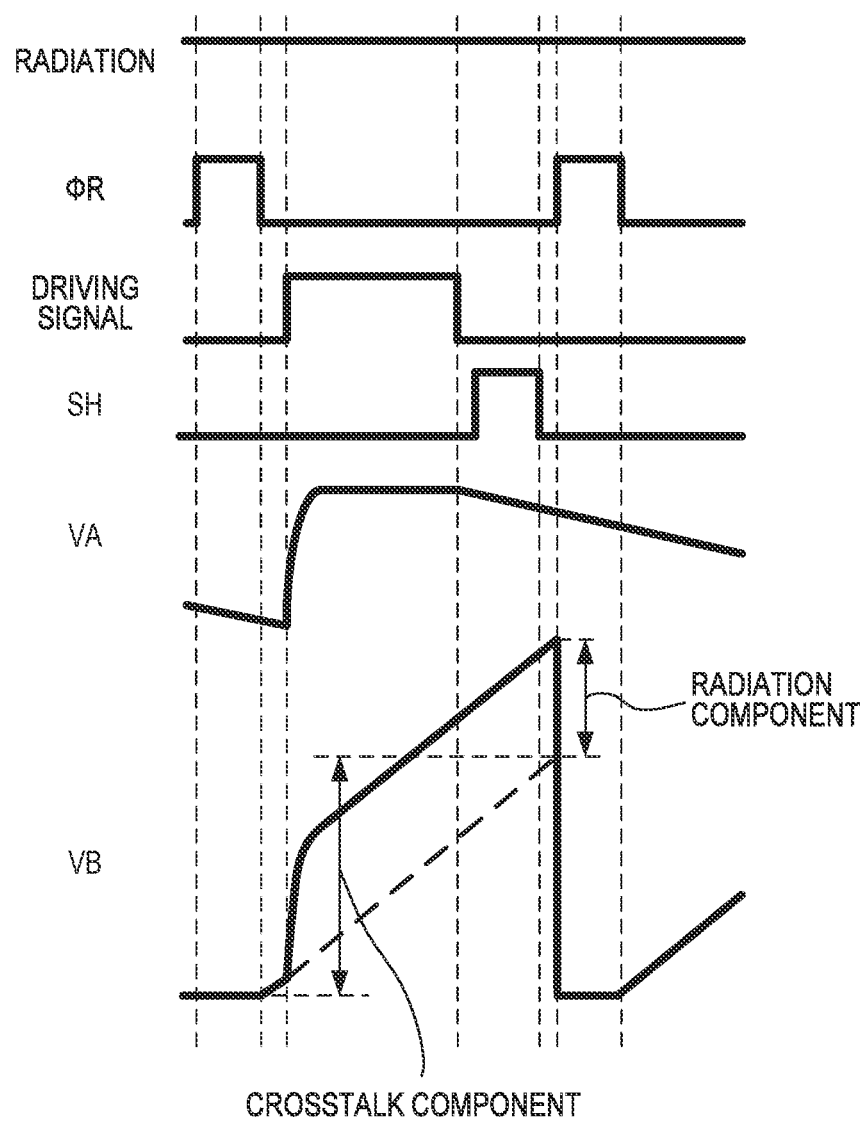
FIG. 14 is a diagram showing a comparative example.
Figure 15:
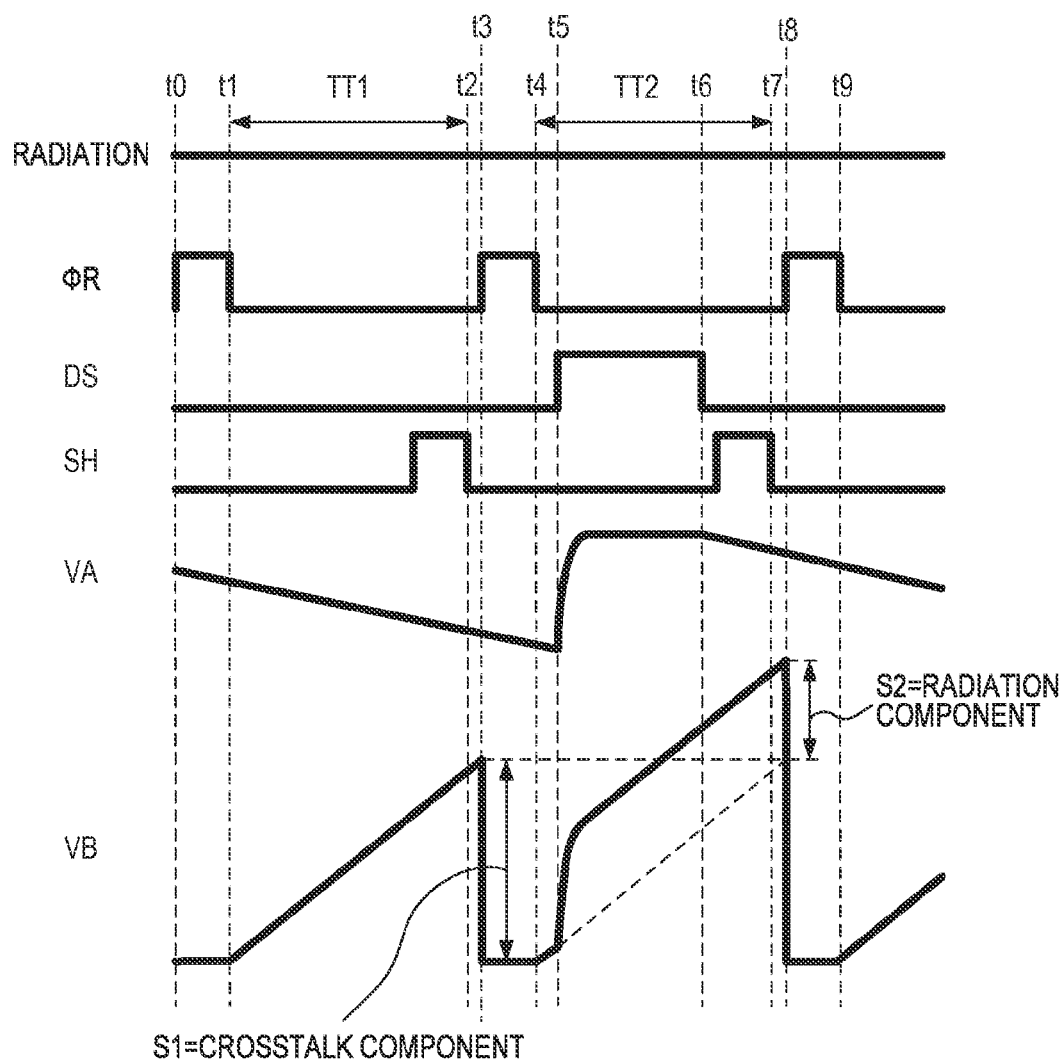
FIG. 15 is a diagram showing operations performed by the radiation imaging apparatus according to the fifth embodiment of the present invention.

A fifth embodiment of the present invention will be described next with reference to FIGS. 13 to 15. The fifth embodiment provides a specific example of the configuration and operations of the readout unit 140. FIG. 13 shows a configuration example of the readout unit 140. FIG. 14 shows a comparative example. FIG. 15 shows an example of operations performed by the readout unit 140 according to the fifth embodiment.

The detecting units 142 of the readout unit 140 each include an amplification circuit AMP, a holding capacitor HC, and a sampling switch SW. The amplification circuit AMP includes a differential amplifier DA that has a first input terminal, a second input terminal, and an output terminal, and a feedback capacitor Cf and reset switch RS that are provided in parallel between the first input terminal and the output terminal. A detection signal line 125 is connected to the first input terminal, and a referential potential REF is supplied to the second terminal. The sampling switch SW is arranged between the output terminal of the differential amplifier DA (amplification circuit AMP) and the holding capacitor HC. VA is the potential of the second electrode 151 of a detecting pixel 121, and VB is the potential of the output terminal of the differential amplifier DA (amplification circuit AMP). The "driving signal" in FIGS. 14 and 15 is a signal that is applied to a driving line 124.

During irradiation of radiation (period T2 in FIG. 4), the potential of the second electrode 151 of the imaging pixels 101 varies. Accompanying this, the potential of the detection signal lines 125 changes due to crosstalk via the parasitic capacitances between the second electrodes 151 and the detection signal lines 125. Accordingly, as illustrated in FIG. 14 (comparative example), the potential VB of the output terminal of the differential amplifier DA (amplification circuit AMP) also varies. In FIG. 14, the "crosstalk component" indicates a change in VB corresponding to a change in the potential of the detection signal line 125 due to crosstalk. Also, the "radiation component" indicates a change in VB corresponding to a change in potential of the detection signal line 125 (i.e., charge accumulated in the second conversion element 122) caused by the second switch 123 being turned on. The "cross talk component" and the "radiation component" are included in the signal accumulated in the holding capacitor HC due to the sampling signal SH being switched to the high level so as to cause the sampling switch SW to turn on.

Operations for reducing the effect of crosstalk will be described below with reference to FIG. 15. First, a reset signal ΦR is switched to the high level at time t0, and a reset switch RS is turned on. Accordingly, VB is reset to the referential potential REF. VB starts to change due to crosstalk at the instant (time t1) that the reset signal ΦR is switched to the low level and the reset switch RS turns off.

Next, sampling is performed on the holding capacitor HC due to the sampling signal SH being switched from the low level to the high level and being furthermore switched from the high level to the low level (until time t2). Accordingly, a signal S1 that corresponds to the crosstalk component is held in the holding capacitor HC. The signal S1 is output via the multiplexer 144 and the AD converter 146.

Next, the reset signal ΦR is switched to the high level at time t3, and the reset switch RS is turned on. Accordingly, VB is reset to the referential potential REF. VB once again starts to change due to crosstalk at the instant (time t4) that the reset signal ΦR is switched to the low level and the reset switch RS turns off.

Next, at times t5 to t6, the second switch 123 turns on due to the potential of the driving line 124 being switched to the high level. At this time, VB changes according to the amount of charge accumulated in the second conversion element 122. Also, irradiation continues even in a state in which the second switch 123 is turned on, and therefore the potential VB continues to change due to crosstalk.

Next, sampling is performed on the holding capacitor HC due to the sampling signal SH being switched from the low level to the high level and being furthermore switched from the high level to the low level (until time t7). Accordingly, a signal S2 that corresponds to the crosstalk component and the radiation component is held in the holding capacitor HC. The signal S2 is output via the multiplexer 144 and the AD converter 146.

By causing the reset switch RS to turn on in the period from time t3 to time t4, the potential of the detection signal line 125 is reset to the referential potential REF, and thereby the crosstalk component in the signal S1 and the crosstalk component in the signal S2 become extremely close in value. Accordingly, the signal processing unit 224 calculates the difference between the signal S2 and the signal S1, whereby it is possible to detect the net radiation component (irradiation amount of radiation), or more specifically, to reduce the crosstalk component. Here, by making TT1 and TT2 in FIG. 15 equal, it is possible to reduce the difference between the crosstalk component in the signal S1 and the crosstalk component in the signal S2.

Here, the signal S1 is a signal that appears in the detection signal line 125 in a state in which the second switch 123 is not caused to turn on after the potential of the detection signal line 125 is reset to the referential potential REF. The signal S2 is a signal that appears in the detection signal line 125 due to the second switch 123 being caused to turn on after the potential of the detection signal line 125 is reset to the referential potential REF.

By removing the crosstalk component as described above, it is possible to detect the irradiation amount of the radiation at a high accuracy. In particular, in detecting the start of irradiation of radiation, detecting the integrated irradiation amount of the radiation (radiation dose), and the like, the signal value is small due to the fact that the signal is read out in a short time. For this reason, removing the crosstalk component is of great significance.

The above-described example is an example in which the difference between the signal S1 and the signal S2 is calculated in the signal processing unit 224, but the differential circuit may be arranged in the readout unit 140, and the signal for the difference between the signal S1 and the signal S2 may be obtained in the readout unit 140.

In the example shown in FIG. 15, in order to sample the signal S1 and the signal S2, the reset switch RS is turned on in the period between t0 and t1 and the period between t3 and t4. Here, KTC noise that is determined at the instant that the reset switch RS is turned off cannot be removed by calculating the difference between signal S1 and signal S2. However, by providing a detection signal line 125 that is different from the column signal line 106, it is possible to reduce the parasitic capacitance of the detection signal line 125, and therefore the KTC noise can be reduced.

Figure 16:
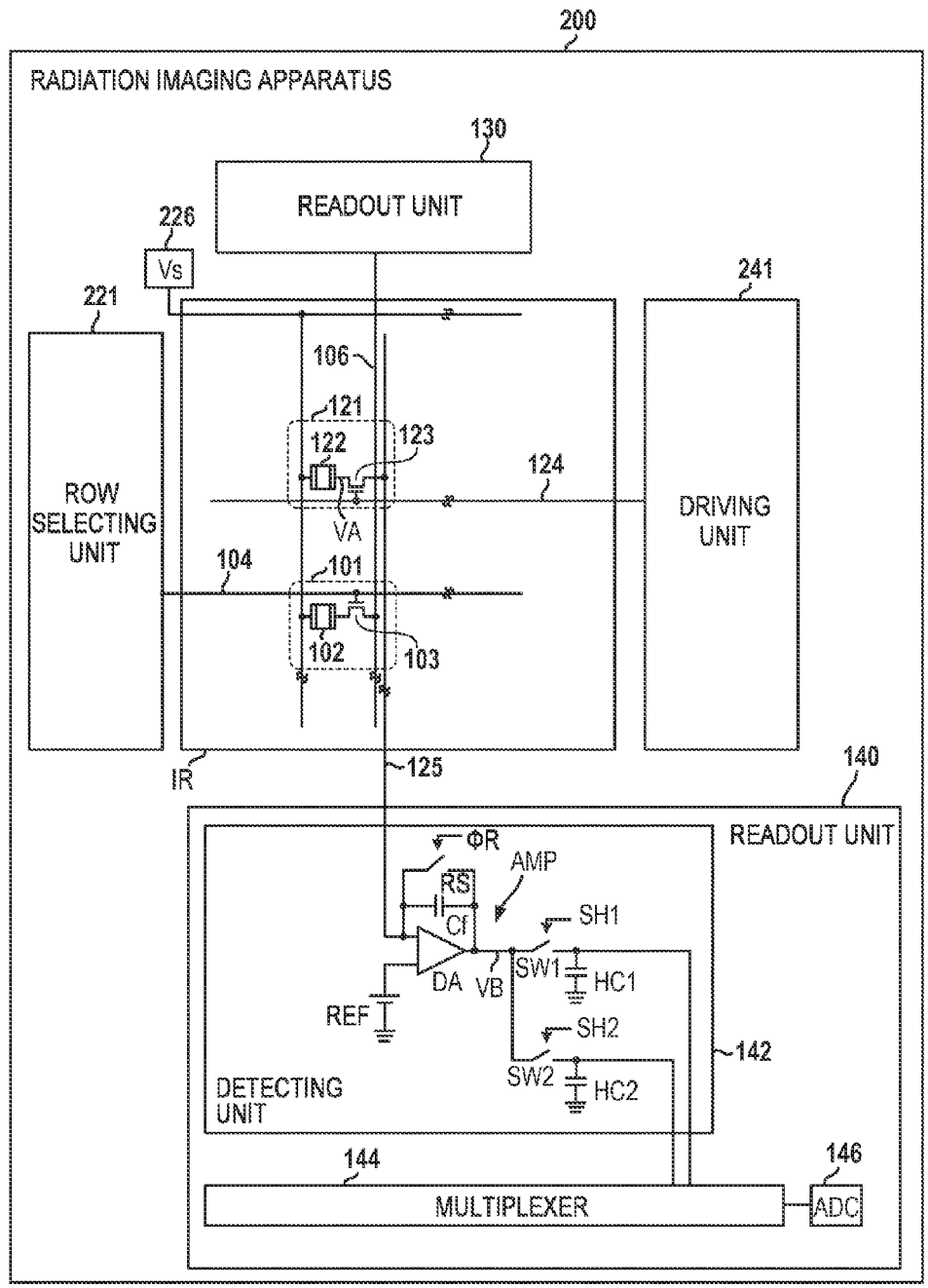
FIG. 16 is a diagram showing a configuration of the radiation imaging apparatus according to a sixth embodiment of the present invention.
Figure 17:
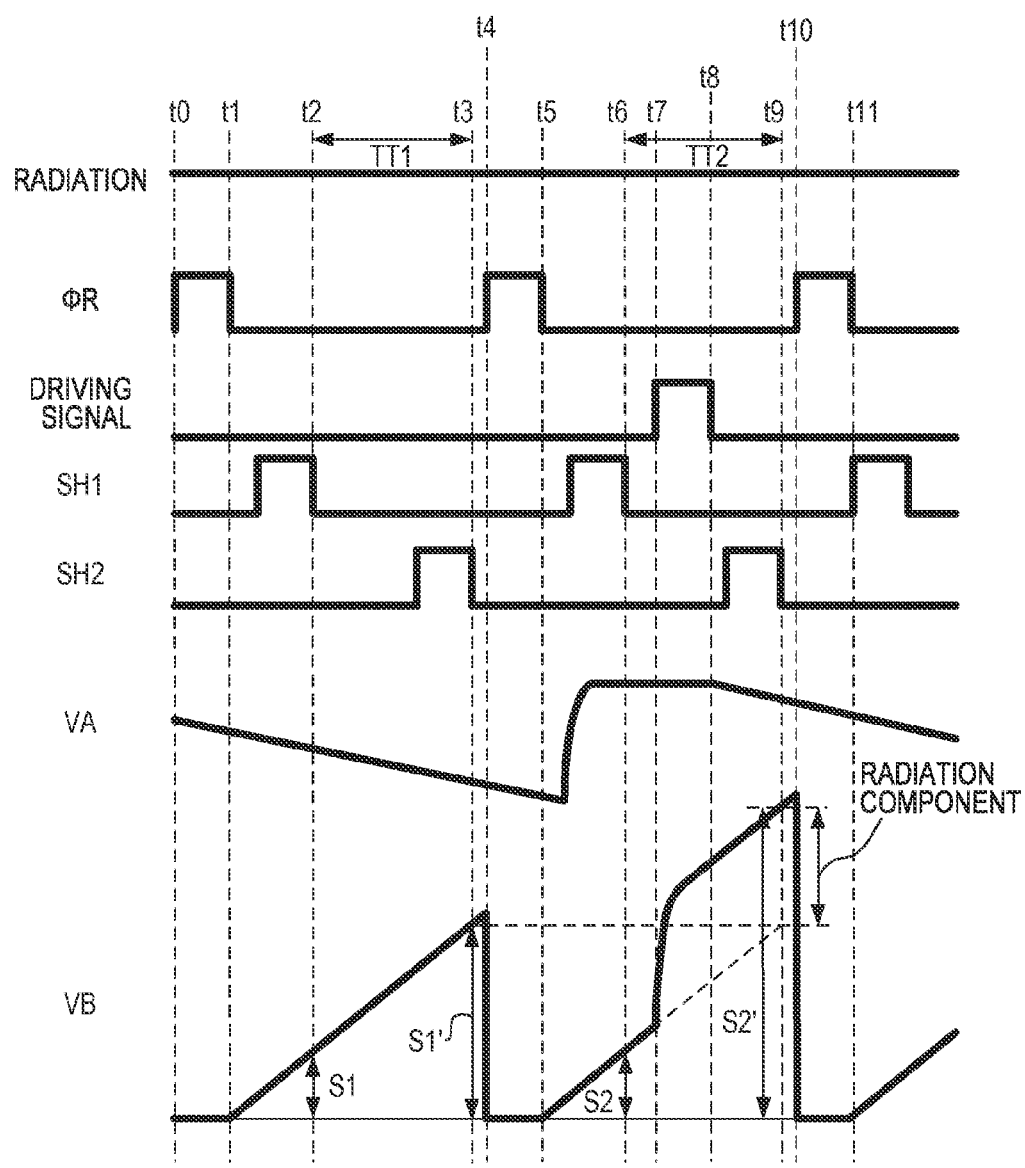
FIG. 17 is a diagram showing operations performed by the radiation imaging apparatus according to the sixth embodiment of the present invention.

A sixth embodiment of the present invention will be described next with reference to FIGS. 16 and 17. The sixth embodiment provides another specific example of the configuration and operations of the readout unit 140. FIG. 16 shows an example of the configuration of the readout unit 140. FIG. 17 shows an example of operations performed by the readout unit 140 according to the sixth embodiment.

In the sixth embodiment, in addition to the amplification circuit AMP, the detecting unit 142 includes a first sampling switch SW1, a second sampling switch SW2, a first holding capacitor HC1, and a second holding capacitor HC2.

First, the reset signal ΦR is switched to the high level at time t0, and the reset switch RS is turned on. Accordingly, VB is reset to the referential potential REF. VB starts to change due to crosstalk at the instant (time t1) that the reset signal ΦR is switched to the low level and the reset switch RS turns off.

Next, sampling is performed on the first holding capacitor HC1 due to a first sampling signal SH1 being switched from the low level to the high level and being furthermore switched from the high level to the low level (until time t2). Accordingly, a signal S1 that corresponds to the crosstalk component at time t2 is held in the first holding capacitor HC1.

Next, sampling is performed on the second holding capacitor HC2 due to a second sampling signal SH2 being switched from the low level to the high level and being furthermore switched from the high level to the low level (until time t3). Accordingly, a signal S1' that corresponds to the crosstalk component at time t3 is held in the second holding capacitor HC2. The signals S1 and S1' are output via the multiplexer 144 and the AD converter 146. A difference S1" between the signal S1' and the signal S1 corresponds to the crosstalk component in period TT1. Also, the difference S1" is a difference resulting from two instances of sampling that each occur after the reset switch RS is turned off, and therefore KTC noise is removed.

Next, the reset signal ΦR is switched to the high level at time t4, and the reset switch RS is turned on. Accordingly, VB is reset to the referential potential REF. VB once again starts to change due to crosstalk at the instant (time t5) that the reset signal ΦR is switched to the low level and the reset switch RS turns off.

Next, sampling is performed on the first holding capacitor HC1 due to the first sampling signal SH1 being switched from the low level to the high level and being furthermore switched from the high level to the low level (until time t6). Accordingly, a signal S2 that corresponds to the crosstalk component at time t6 is held in the first holding capacitor HC1.

Next, in the period from time t7 to time t8, the second switch 123 is turned on due to the potential of the driving line 124 being switched to the high level. At this time, VB changes according to the amount of charge accumulated in the second conversion element 122. Also, irradiation continues even in a state in which the second switch 123 is turned on, and therefore the potential VB continues to change due to crosstalk.

Next, sampling is performed on the second holding capacitor HC2 due to the second sampling signal SH2 being switched from the low level to the high level and being furthermore switched from the high level to the low level (until time t9). Accordingly, a signal S2' that corresponds to the crosstalk component at time t9 is held in the second holding capacitor HC2. The signals S2 and S2' are output via the multiplexer 144 and the AD converter 146. A difference S2" between the signal S2' and the signal S2 corresponds to the crosstalk component and the radiation component in period TT2. Also, the difference S2" is a difference resulting from two instances of sampling that each occur after the reset switch RS is turned off, and therefore KTC noise is removed.

By causing the reset switch RS to turn on in the period from time t4 to time t5, the potential of the detection signal line 125 is reset to the referential potential REF, and thereby the crosstalk component in the difference S1" and the crosstalk component in the difference S2" become extremely close in value. Accordingly, the signal processing unit 224 calculates the difference between the difference S2" and the difference S1", whereby it is possible to detect the net radiation component (irradiation amount of radiation), or more specifically, to reduce the crosstalk component. Also, the differences S1" and S2" do not include the KTC noise, and therefore the difference between the difference S2" and the difference S1" also does not include the KTC noise. Here, by making TT1 and TT2 in FIG. 17 equal, it is possible to reduce the difference between the crosstalk component in the difference S1" and the crosstalk component in the difference S2".

The above-described example is an example of calculating a difference between signals in the signal processing unit 224, but it is possible to arrange a differential circuit in the readout unit 140 and obtain a signal for the difference between the signals in the readout unit 140.

Here, the difference S1" is the amount of change in the signal that appears in the detection signal line 125 in a state in which the second switch 123 is not caused to turn on after the potential of the detection signal line 125 is reset to the referential potential REF. Here, the difference S2" is the amount of change in the signal that appears in the detection signal line 125 when the second switch 123 is changed from the off state to the on state after the potential of the detection signal line 125 is reset to the referential potential REF.

A seventh embodiment of the present invention will be described next with reference to FIGS. 18, 19A, and 19B. FIG. 18 shows a configuration of the radiation imaging apparatus according to the seventh embodiment. The radiation imaging apparatus 200 according to the seventh embodiment has multiple pixels that are arrayed in an imaging area IR so as to form multiple rows and multiple columns. The multiple pixels include multiple imaging pixels 101 for obtaining a radiation image, and a detecting pixel 121 for detecting radiation. The multiple pixels can be arrayed on the support substrate 100. The imaging pixels 101 each include a first conversion element 102 that converts radiation into an electrical signal, and a first switch 103 that is arranged between a column signal line 106 and the first conversion element 102. The detecting pixels 121 each include a second conversion element 122 that converts radiation into an electrical signal, a second switch 123 that is arranged between a detection signal line 125 and the second conversion element 122, and a third switch 126 that is arranged between a column signal line 106 and the second conversion element 122.

In the seventh embodiment, for each imaging, it is possible to select whether the detecting pixels 121 are to be used for detecting radiation or are to be used for obtaining an image.

In the case of performing detection of radiation, the radiation detection areas (ROI), which area the regions in which radiation is monitored, can change according to the site being imaged. For this reason, detecting pixels 121 that are not arranged in the radiation detection area (ROI) can be used for detecting an image signal.

Before imaging is performed, the radiation detection areas (ROI), which are the areas in which radiation is monitored, are determined based on information input into the controller 1002, and that information is sent to the radiation imaging apparatus 200 via the interface 1003. Then, by changing the operation methods for the detecting pixels 121 arranged in the ROI and the detecting pixels 121 arranged outside of the ROI, the detecting pixels 121 are given different functions.

FIGS. 19A and 19B illustrate operations of the seventh embodiment of the present invention. FIG. 19A shows operations in the case where a detecting pixel 121 is used for detecting radiation, and FIG. 19B shows operations in the case where a detecting pixel 121 is used for obtaining an image.

Period T1 is a period of waiting for the start of irradiation of radiation, similarly to FIG. 4 of the first embodiment. In period T1, the operations of a detecting pixel 121 are the same in the case of being used for detecting radiation and in the case of being used for obtaining an image. In period T1, the voltage Vg of the first driving line 104 is periodically switched to the high level in order to remove dark currents that are generated in the conversion elements 102 of the imaging pixels 101. Accordingly, the conversion element 102 is electrically connected to the column signal line 106, which is fixed at a constant voltage. This operation prevents the charge resulting from the dark currents from being accumulated over a long time in the conversion elements 102. Also, in order to detect the start of irradiation of radiation, in period T1, the voltage Vd of the second driving line 124 that drives the detecting pixel 121 is fixed at the high level, and the second switch 123 of the detecting pixel 121 is fixed in the on state. The signal read out by the readout unit 140 from the detecting pixel 121 is processed by the signal processing unit 224, and thus the start of irradiation of radiation is detected. When the start of irradiation of radiation is detected, period T2 is entered.

Period T2 is a period during which radiation is emitted, similarly to FIG. 4 in the first embodiment. Period T2 is also a period during which the irradiation amount of radiation is detected. In period T2 and onward, the operations of the detecting pixel 121 are different in the case of being used for detecting radiation and in the case of being used for obtaining an image.

With the detecting pixel 121 that is used for detecting radiation, in period T2, during irradiation of radiation, the second switch 123 is turned on due to the corresponding second driving line 124 being intermittently switched to the high level, as shown in FIG. 19A. According to this operation, the electrical signal resulting from conversion performed by the conversion element 122 of the detecting pixel 121, or in other words, the signal corresponding to the irradiation amount of radiation is read out by the readout unit 140 via the second switch 123 and the detection signal line 125. When the irradiation amount of radiation has reached an appropriate irradiation amount, the control unit 224 sends the exposure stop signal to the radiation source interface 1004 via the interface 1003 based on the read-out signal.

In period T3, the signal is read out by the readout unit 130 when the first driving line 104 is switched to the high level. Here, the signal of the conversion element 122 of the detecting pixel 121 is read out in the period T2. Accordingly, in the period T3, regarding the signal of the conversion element 122 of the detecting pixel 121, only signals that correspond to the charge accumulated in the conversion element 122 after the reading out in period T2 are read out by the readout unit 130 via the third switch 126 and the column signal line 106.

On the other hand, with the detecting pixel 121 that is used for obtaining an image, the corresponding second driving line 124 is not driven to the high level in period T2, as shown in FIG. 19B. Accordingly, the charge generated by the conversion element 122 is stored in the detecting pixel 121 that is used for obtaining an image. Accordingly, in period T3, which is the pixel readout period, the signal is read out by the readout unit 130 via the column signal line 106 due to the first driving line 104 being driven to the high level and the third switch 126 turning on.

As described above, in the seventh embodiment, the detecting pixel 121 can be used as a pixel for detecting radiation and can be used as a pixel for obtaining an image. Accordingly, if it is determined that the detecting pixel 121 does not need to be used for radiation detection according to the imaging site, the image signal can be obtained from the pixel portion of the detecting pixel 121 as well by performing driving for obtaining an image. If no signal for obtaining an image is read out from the detecting pixel 121, it is not necessary to generate a signal at the position of the detecting pixel 121 based on the pixel signal of the imaging pixels 101 in the periphery of the detecting pixel 121. However, in the seventh embodiment, it is possible to read out the true signal from the detecting pixel 121 in which the driving method for obtaining an image was performed.

Also in the case where the detecting pixel 121 is used for detecting radiation, after detection of the time at which radiation is to be stopped, the signal corresponding to the radiation dose emitted in the period until the radiation is actually stopped can be read out by the readout unit 130 via the third switch 126 and the column signal line 106. Since this signal amount can also be allowed to contribute to the reconstruction of the image, it is possible to predict the signal amount with greater precision than predicting the actual signal amount using the signals of only the peripheral pixels.

Also, in the seventh embodiment, it is possible to freely select whether a detecting pixel 121 is to be used for obtaining an image or is to be used for detecting radiation, and therefore it is also possible to increase the number of pixels used for detecting radiation according to the radiation detection amount during radiation irradiation.

Figure 20A:
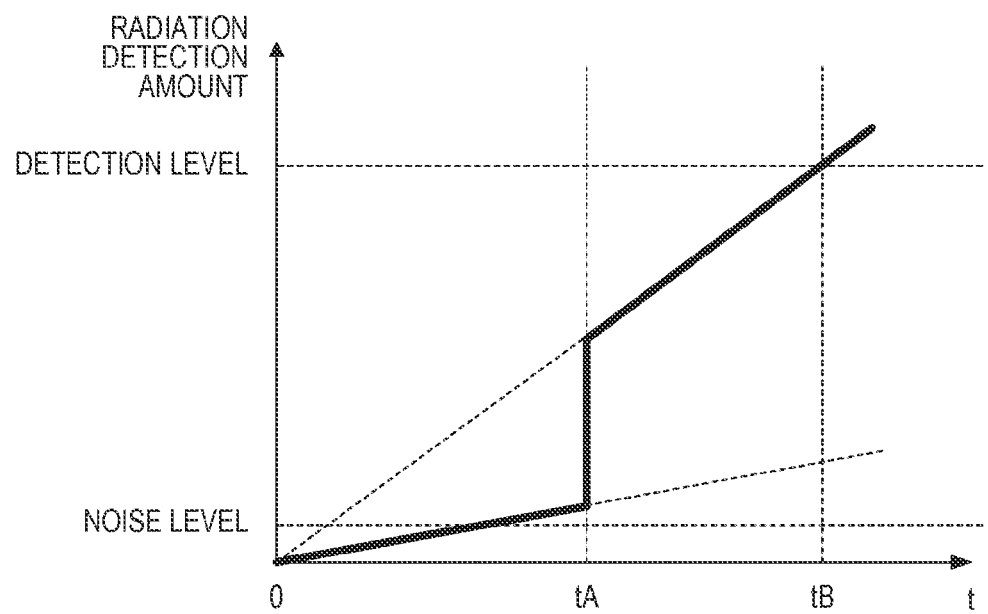
FIGS. 20A and 20B are diagrams showing a usage example of the radiation imaging apparatus according to the seventh embodiment of the present invention.
Figure 20B:
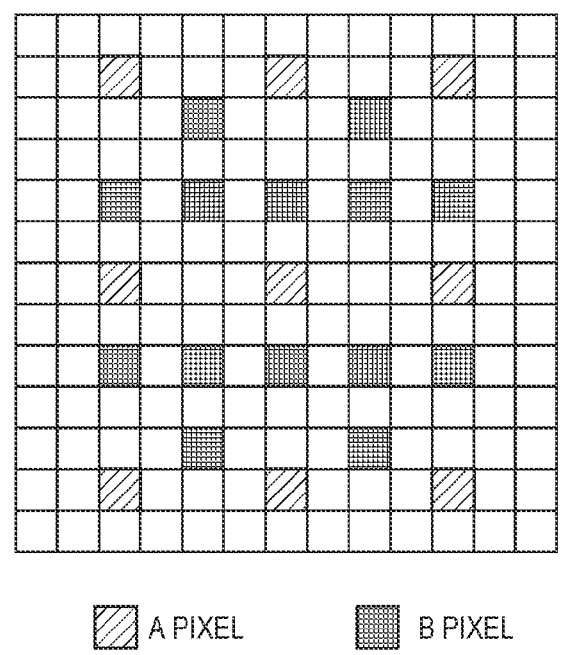

An example of increasing the number of pixels used for detecting radiation during irradiation of radiation will be described with reference to FIGS. 20A and 20B. Note that A pixel and B pixel are detecting pixels 121. For example, only the A pixels in FIG. 20B are used for radiation detection in the period from time 0 to time $t_A$ in FIG. 20A. In the case where only the A pixels are used, as shown in FIG. 20A, if the small signal amount is small and only signals around the noise level can be obtained, the radiation amount cannot be accurately detected in some cases. For this reason, it is possible to increase the sensitivity of detecting the irradiation amount of radiation by, for example, switching the B pixels in FIG. 20B to pixels that are used for detection of the radiation irradiation amount as well. At time $t_A$ in FIG. 20A, the detection sensitivity is increased by using a configuration in which the A pixels and the B pixels in FIG. 20B can be used as the pixels used for detecting the radiation amount. Also, at time $t_B$, the radiation irradiation amount reaches a determination level, and the detection of the irradiation amount can be accurately detected. In the case of changing the B pixels to pixels for detecting radiation at a point after the start of detection as well, the B pixels have accumulated the charges generated by the conversion elements due to radiation irradiation, and therefore it is possible to accurately detect the radiation irradiation amount.

As described above, the number of pixels used for radiation detection is changed (optimized) in accordance with the intensity of the radiation and the detection sensitivity is adjusted, whereby the irradiation amount can be accurately detected. According to a configuration according to which the optimal number can be set by matching the number of pixels used in detection to the irradiation intensity of radiation, the number of pixels 121 used needlessly for detecting radiation can be reduced. Also, it is possible to increase the number of pixels 121 used for obtaining an image, and to obtain a more accurate radiation image.

Also, in the seventh embodiment, although the operations started in period T1, which is for detection of the start of irradiation of radiation, the operations may start in period T2 if the start of irradiation of radiation does not need to be determined.

Figure 21:
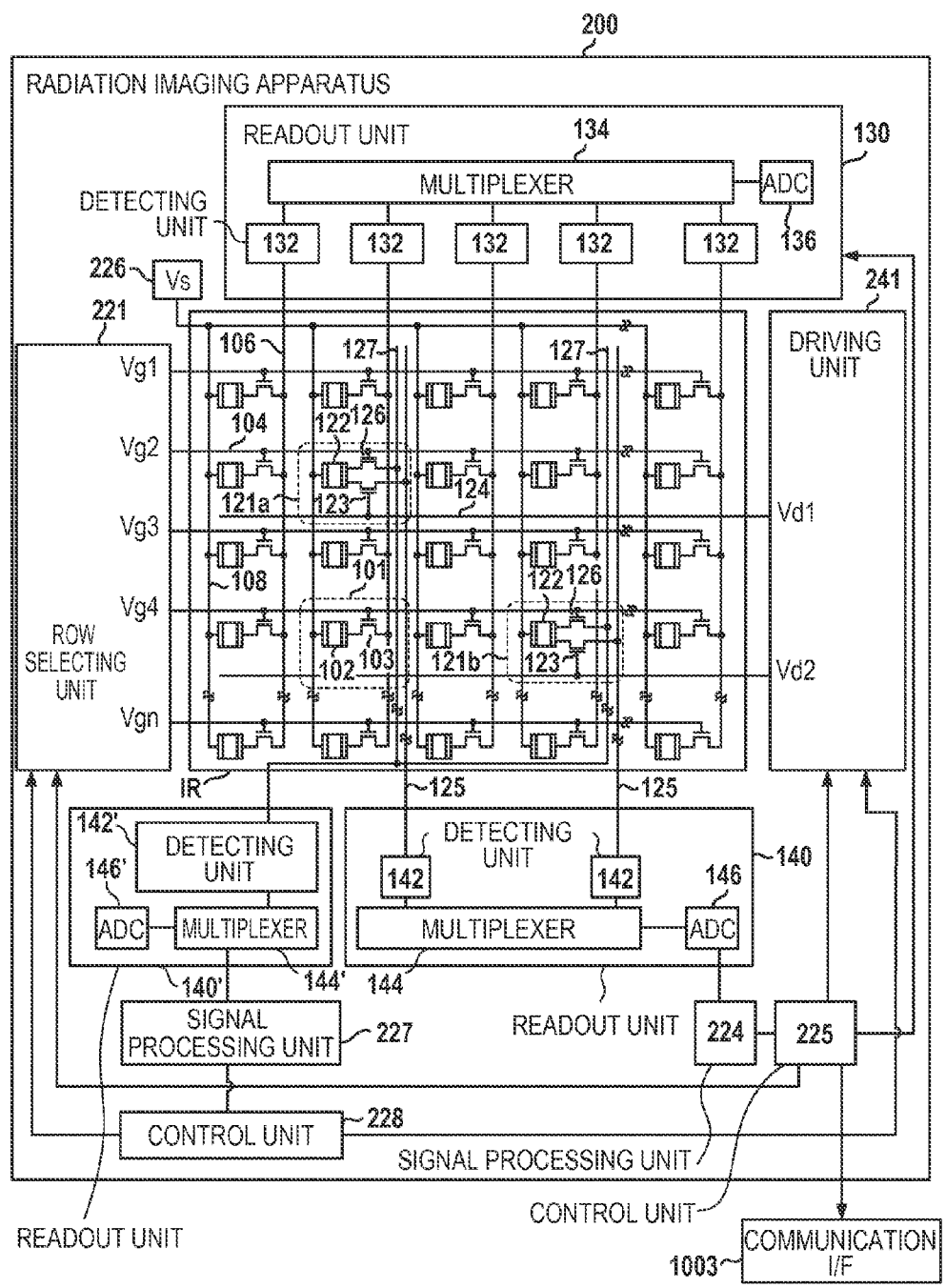
FIG. 21 is a diagram showing a configuration of the radiation imaging apparatus according to an eighth embodiment of the present invention.

An eighth embodiment of the present invention will be described next with reference to FIGS. 21 to 22. FIG. 21 shows a configuration of the radiation imaging apparatus 200, which is the eighth embodiment of the present invention. In the eighth embodiment, it is possible to detect whether or not any detecting pixel 121 is to be used for detecting the start of irradiation of radiation and for detecting the irradiation amount of radiation.

In the seventh embodiment, the third switches 126 of the detecting pixels 121 are connected to the column signal lines 106, whereas in the eighth embodiment, the third switches 126 are connected to second detection signal lines 127. Third driving lines 128 are connected to the third switches 126. Also, the second detection signal lines 127 are connected to a readout unit 140'. The readout unit 140' can include multiple detecting units 142', a multiplexer 144', and an AD converter 146'. The detecting units 142' each include a differential amplifier, for example. The multiplexer 144' supplies the signal from the detecting unit 142' to the AD converter 146'. The AD converter 146' converts the supplied signal into a digital signal and outputs it.

The output of the readout unit 140' (AD converter 146') is supplied to a signal processing unit 227 and is processed by the signal processing unit 227. Based on the output of the readout unit 140' (AD converter 146'), the signal processing unit 227 outputs information indicating irradiation of radiation on the radiation imaging apparatus 200. Specifically, the signal processing unit 227 detects irradiation of radiation on the radiation imaging apparatus 200, for example. The control unit 228 controls the row selecting unit 221 and the driving unit 241 based on the information from the signal processing unit 227. Based on the information from the signal processing unit 227, the control unit 228 performs detection of the start of irradiation of radiation and controls the start of accumulation of charges corresponding to the emitted radiation in the imaging pixels 101.

A driving method according to the eighth embodiment will be described with reference to FIG. 22. FIG. 22 shows an example in which, as an example, a detecting pixel 121a is used as a pixel for detecting the start of irradiation of radiation, and a detecting pixel 121b is used as a pixel for detecting the radiation dose.

Period T1 is a period of waiting for the start of irradiation of radiation. Specifically, period T1 is from when the power source of the radiation imaging apparatus 200 is switched on and imaging of a radiation image becomes possible until when the exposure switch of the radiation source 1005 is operated and the irradiation of radiation is detected. In order to remove dark currents that are generated in the conversion elements 102 of the imaging pixels 101 and in the conversion elements 122 of the detecting pixels 121b used for imaging, the conversion elements 102 and 122 are periodically reset to a fixed potential. Specifically, the voltages Vg1 to Vgn of the first driving lines 104 are switched to the high level in sequence, and the conversion elements 102 are electrically connected to the column signal lines 106, which are fixed at a constant voltage. Also, the voltage Vd2 of the second driving lines 124 connected to the detecting pixels 121 that are not used for detecting the start of irradiation of radiation are switched in sequence to the high level, and the conversion elements 122 in the detecting pixels 121b are connected to the first detection signal lines 125, which are fixed at a constant voltage. This prevents the charge resulting from the dark currents from being accumulated over a long time in the conversion elements 102 of the imaging pixels 101 and the conversion elements 122 of the detecting pixels 121b.

On the other hand, with the detecting pixels 121a used for detecting radiation, in period T1, the voltage Va1 of the third driving lines 128 is fixed at the high level, and the third switches 126 are fixed in the on state. The signals read out by the readout unit 140' from the detecting pixels 121a via the second detection signal lines 127 are processed by the signal processing unit 227, and the start of irradiation of radiation is detected. When the start of irradiation of radiation is detected, period T2 is entered.

In period T2, the voltage Vd1 of the second driving lines 124 connected to the pixels 121b that are used for detecting the radiation irradiation amount is intermittently switched to the high level. According to this, similarly to the other embodiments, when the radiation irradiation amount is detected and it is detected that an appropriate irradiation amount has been reached, the irradiation of radiation is stopped, and period T3 is entered.

In period T3, the voltages Vg1 to Vgn of the first driving lines 104 are switched to the high level in sequence and the conversion elements 102 are electrically connected to the column signal lines 106, which are fixed at a constant voltage, and thereby the image signals are read out by the readout unit 130.

According to the eighth embodiment, any detecting pixel 121 can be used for detecting the start of irradiation of radiation, and any detecting pixel 121 can be used for detecting the radiation irradiation amount. For this reason, usage according to which only some areas are used for detecting the start of irradiation of radiation is possible.

In detecting the start of irradiation of radiation, improvement of the SNR and high-speed readout are extremely important. For example, if detection is performed in only portions strongly exposed to radiation, such as directly-exposed portions, using the eighth embodiment, it is possible to reduce the parasitic capacitances of the detection signal lines 127 while ensuring the sensitivity. This is because the detecting pixels 121 that are not exposed to much radiation are not connected to the second detection signal lines 127. For this reason, it is possible to realize an improvement in the SNR by reducing noise, high-speed readout by shortening the reset time, and the like.

Also, in the eighth embodiment, when detection of the start of irradiation of radiation is to be performed, there is no need to allow readout units other than the readout unit 140', namely the readout unit 130 and the readout unit 140, to operate. Also, it is possible to use the second detection signal lines 127 to read out the charges accumulated in the pixels 121 in bundles. For example, if multiple second detection signal lines are bundled into one, the readout unit 140' does not need to allow multiple ICs to operate, and it is possible to suppress power consumption for performing detection of the start of irradiation of radiation. The time before the start of irradiation of radiation sometimes exceeds 10 minutes depends on the method of use, and therefore it is extremely important to suppress the power consumption.

Figure 22:
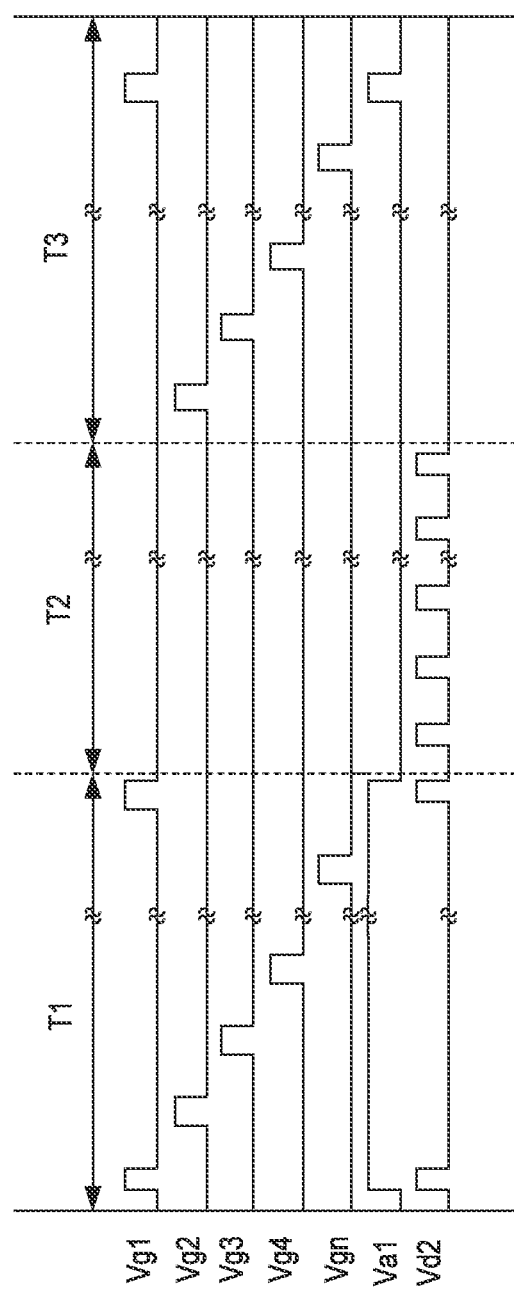
FIG. 22 is a diagram showing operations of the radiation imaging apparatus according to the eighth embodiment of the present invention.

Also, although FIG. 22 shows an example in which the detecting pixels 121a are used only for detecting the start of irradiation of radiation, it is also possible to use the detecting pixels 121a for detecting the radiation dose in period T2 after being used for detecting the start of irradiation.

Figure 23:
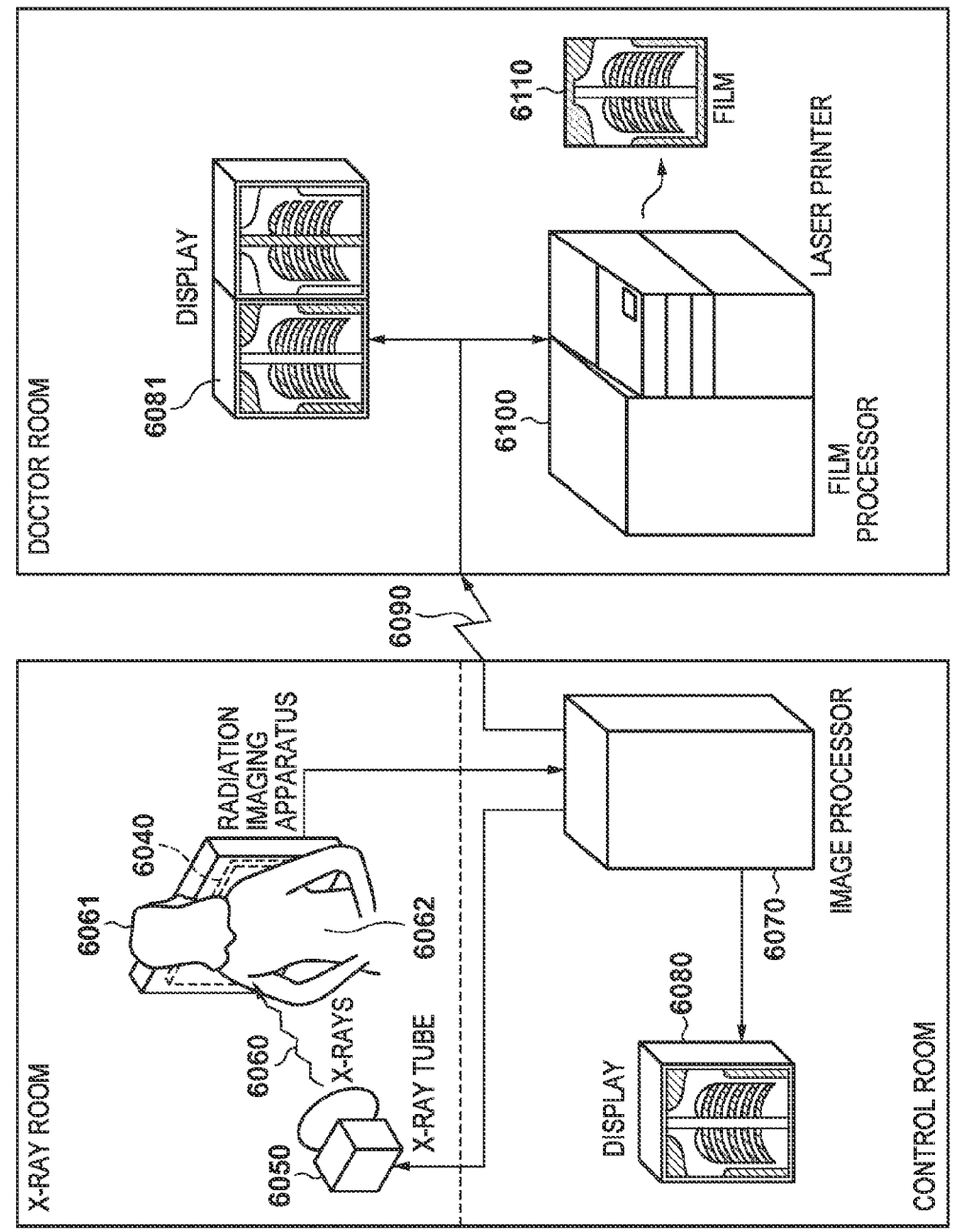
FIG. 23 is a diagram showing an example of a configuration of a radiation detection system.

Hereinafter, with reference to FIG. 23, an example will be described in which the radiation imaging apparatus 200 is applied to a radiation detection system. X-rays 6060 emitted by an X-ray tube 6050, which is a radiation source, pass through a chest portion 6062 of a patient or examination subject 6061 and are incident on a radiation imaging apparatus 6040, which is represented by the above-described radiation imaging apparatus 200. The received X-rays include information about the interior of the body of the examination subject 6061. The scintillator 216 emits light in correspondence with the incident X-rays, the light is photoelectrically converted using photoelectric conversion elements, and thereby electrical information is obtained. This information is digitally converted, subjected to image processing by an image processor 6070, which is a signal processing means, and can be observed using a display 6080, which is a display means in a control room.

Also, the information can be transferred to a remote location by a transfer processing means such as a telephone line 6090, can be displayed on a display 6081, which is a displaying means, in a doctor room or the like at the other location, or stored in a storing means such as an optical disk, and a doctor at the remote location can also perform diagnosis. The information can also be recorded on film 6110, which is a recording medium, by a film processor 6100, which is a recording means.

Embodiments of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application Nos. 2014-094875, filed May 1, 2014 and 2015-060021, filed Mar. 23, 2015, which are hereby incorporated by reference herein in their entirety.

What is claimed is:

1. A radiation imaging apparatus comprising:
    an imaging area in which a plurality of imaging pixels for obtaining a radiation image are arranged to form a plurality of rows and a plurality of columns, each of the plurality of imaging pixels including a first conversion element configured to convert radiation into an electrical signal, and a first switch;
    a plurality of first driving lines for driving the first switches of the plurality of imaging pixels;
    a plurality of column signal lines arranged to respectively correspond to the plurality of columns such that signals are read out from the plurality of imaging pixels;
    a plurality of detecting pixels each arranged in a position which is specified by a row of the plurality of rows and a column of the plurality of columns, the detecting pixel being used for at least one of (a) detecting start of irradiation of radiation and (b) monitoring irradiation amount of radiation, and each of the plurality of detecting pixels including a second conversion element configured to convert radiation into an electrical signal, and a second switch;
    a plurality of second driving lines which are different from the plurality of first driving lines, wherein at least one of the plurality of second driving lines is supplied with a signal including, in a period during which radiation is irradiated, a level for turning on the second switch and a level for turning off the second switch; and
    a plurality of detection signal lines which are different from the plurality of column signal lines, each of the plurality of detection signal lines corresponding to at least one of to the plurality of detecting pixels,
    wherein each of the first switches is electrically connected to a corresponding first conversion element and a corresponding column signal line among the plurality of column signal lines, and is not electrically connected to the detection signal line, and wherein each of the plurality of second switches has a control terminal connected to a corresponding second driving line of the plurality of second driving lines, each of the second switches is electrically connected to a corresponding second conversion element and a corresponding detection signal line of the plurality of detection signal lines and is not electrically connected to the plurality of column signal lines.

2. The radiation imaging apparatus according to claim 1, wherein in an orthogonal projection on a surface parallel to the imaging area, the detection signal line and the first conversion element do not overlap and the detection signal line and the second conversion element do not overlap.

3. The radiation imaging apparatus according to claim 1, wherein the plurality of columns includes a column in which the column signal line and the detection signal line are arranged, and a column in which the column signal line and a dummy detection signal line, to which neither the first switch nor the second switch are electrically connected, are arranged.

4. The radiation imaging apparatus according to claim 3, wherein a fixed potential is applied to the dummy detection signal line.

5. The radiation imaging apparatus according to claim 4, further comprising:
    a detecting unit configured to detect irradiation of radiation to the imaging area based on an electrical signal that appears in the dummy detection signal line.

6. The radiation imaging apparatus according to claim 1, wherein the plurality of rows include a row in which the first driving line and the first driving line for driving the second switch are arranged, and a row in which a driving line and a dummy driving line to which neither the first switch nor the second switch are electrically connected, are arranged.

7. The radiation imaging apparatus according to claim 6, wherein a fixed potential is provided to the dummy driving line.

8. The radiation imaging apparatus according to claim 6, further comprising:
a detecting unit configured to detect irradiation of radiation to the imaging area based on an electrical signal that appears in the dummy driving line.

9. The radiation imaging apparatus according to claim 1, wherein
the plurality of columns includes a column in which the column signal line and the detection signal line are arranged, and a column in which the column signal line and a dummy detection signal line, to which neither the first switch nor the second switch are electrically connected, are arranged,
the plurality of rows includes a row in which a first driving line of the plurality of first driving lines and the second driving line are arranged, and a row in which another first driving line of the plurality of first driving lines and a dummy driving line to which neither the first switch nor the second switch are electrically connected, are arranged, and
the dummy detection signal line and the dummy driving line are connected to each other.

10. The radiation imaging apparatus according to claim 9, wherein the dummy detection signal line and the dummy driving line are connected in an area outside of the imaging area.

11. The radiation imaging apparatus according to claim 1, wherein the imaging area is composed of a plurality of unit areas arrayed so as to form a grid, and the plurality of unit areas are formed by unit areas each of which includes, out of the plurality of imaging pixels and the detecting pixel, one of the plurality of imaging pixels, and a unit area that includes both one of the plurality of imaging pixels and the detecting pixel.

12. The radiation imaging apparatus according to claim 1, further comprising:
a detecting unit configured to detect an irradiation amount of radiation based on an electrical signal that appears in the detection signal line.

13. The radiation imaging apparatus according to claim 12, wherein the detecting unit detects an irradiation amount of radiation based on a difference between a signal that appears in the detection signal line in a state in which the second switch is not caused to turn on after the potential of the detection signal line is reset, and a signal that appears in the detection signal line due to the second switch being caused to turn on after a potential of the detection signal line is reset.

14. The radiation imaging apparatus according to claim 12, wherein the detecting unit detects an irradiation amount of radiation based on a difference between an amount of change in a signal that appears in the detection signal line in a state in which the second switch is not caused to turn on after the potential of the detection signal line is reset, and an amount of change in a signal that appears in the detection signal line when the second switch is changed from an off state to an on state after a potential of the detection signal line is reset.

15. The radiation imaging apparatus according to claim 1, wherein in a period of detecting that irradiation of radiation has started, the second switch is fixed in an on state, and in a period during which an irradiation amount of radiation is monitored, the second switch is intermittently switched to the on state.

16. The radiation imaging apparatus according to claim 1, wherein each of the plurality of detecting pixels further includes a third switch arranged between a corresponding second conversion element and one of the plurality of column signal lines.

17. The radiation imaging apparatus according to claim 16, wherein
during irradiation of radiation, the second switch of one or more of the plurality of detecting pixels is not turned on, and
after irradiation of radiation ends, an image signal is obtained based on a signal read out from the one or more of the plurality of detecting pixels via the column signal line by causing the third switch to turn on.

18. The radiation imaging apparatus according to claim 16, wherein
during irradiation of radiation, the number of the detecting pixels, among the plurality of detecting pixels, for performing detection of radiation is changed by causing the second switches of the detecting pixels to turn on.

19. The radiation imaging apparatus according to claim 16, wherein the first switch is driven by the first driving line, the second switch is driven by the second driving line, and the third switch is driven by a third driving line.

20. A radiation imaging system, comprising:
a radiation source configured to generate radiation; and
the radiation imaging apparatus according to claim 1.

21. The radiation imaging apparatus according to claim 1, wherein the detection signal line is arranged between two of the plurality of column signal line.

22. The radiation imaging apparatus according to claim 1, wherein the second driving line is connected to a driving unit configured to drive the driving line in the period during which radiation is irradiated.

23. The radiation imaging apparatus according to claim 1, wherein the plurality of column includes a column in which the detection signal line and one of the plurality of column signal line are arranged.

* * * * *